United States Patent
Ricci et al.

(10) Patent No.: US 11,333,648 B1
(45) Date of Patent: May 17, 2022

(54) DECOUPLED THERMODYNAMIC SENSING SYSTEM

(71) Applicant: PGR Holdings, LLC, Narragansett, RI (US)

(72) Inventors: Peter P. Ricci, West Warwick, RI (US); Otto J. Gregory, Narragansett, RI (US)

(73) Assignee: PGR Holdings, LLC, Narragansett, RI (US)

( * ) Notice: Subject to any disclaimer, the term of this patent is extended or adjusted under 35 U.S.C. 154(b) by 0 days.

(21) Appl. No.: 17/453,620

(22) Filed: Nov. 4, 2021

Related U.S. Application Data

(60) Provisional application No. 63/110,829, filed on Nov. 6, 2020.

(51) Int. Cl.
*G01N 33/00* (2006.01)
*G01K 17/06* (2006.01)

(52) U.S. Cl.
CPC ......... *G01N 33/0013* (2013.01); *G01K 17/06* (2013.01)

(58) Field of Classification Search
CPC ........................... G01N 33/0013; G01K 17/06
USPC ................................ 73/31.01, 31.02, 31.03
See application file for complete search history.

(56) References Cited

U.S. PATENT DOCUMENTS

| | | | | |
|---|---|---|---|---|
| 4,030,340 A | * | 6/1977 | Chang | G01N 27/12 73/31.06 |
| 4,542,640 A | * | 9/1985 | Clifford | G01N 27/122 73/31.06 |
| 5,137,924 A | | 8/1992 | Short et al. | |
| 5,501,297 A | * | 3/1996 | Josephs | B66F 9/07545 187/222 |

(Continued)

FOREIGN PATENT DOCUMENTS

| DE | 4334410 | * | 4/1995 |
|---|---|---|---|
| JP | 2001250909 A | | 9/2001 |

(Continued)

OTHER PUBLICATIONS

Aguilar, et al., A Hybrid Nanosensor for TNT Vapor Detection, Nano Letters, 10(2):380-384 (Feb. 2010).

(Continued)

*Primary Examiner* — Daniel S Larkin
(74) *Attorney, Agent, or Firm* — Eversheds Sutherland (US) LLP; Christopher C. Bolten; Regis C. Worley, Jr.

(57) ABSTRACT

Ultrasensitive, decoupled thermodynamic sensing platforms for the detection of chemical compounds in the vapor phase at trace levels are disclosed, wherein the sensors have a heating resistor decoupled from a sensing resistor. Embodiments of the decoupled sensor comprise a metallic microheater resistor on one side of substrate, and a sensor resistor coupled to a catalyst on the other side of the substrate. A sensor array may be provided including a plurality of sensors each having a different catalyst that, when exposed to an analyte, each experience an endothermic reaction, an (Continued)

exothermic reaction, or no reaction. A comparison of the reaction results to data comprising previously obtained reaction results may be used to determine the presence and the identity of the analyte. Advantageously, the decoupled sensors utilize less power and provide greater sensitivity than other known systems, and may be used to detect and identify a single molecule of an analyte.

30 Claims, 9 Drawing Sheets

(56) References Cited

U.S. PATENT DOCUMENTS

| | | | |
|---|---|---|---|
| 5,541,851 A * | 7/1996 | Sato | G01N 33/0031 700/266 |
| 5,731,510 A * | 3/1998 | Jones | G01N 29/228 73/23.31 |
| 5,997,832 A | 12/1999 | Lieber et al. | |
| 6,171,378 B1 | 1/2001 | Manginell et al. | |
| 7,147,695 B2 | 12/2006 | Mitra | |
| 7,329,389 B2 | 2/2008 | Horovitz et al. | |
| 7,581,434 B1 | 9/2009 | Discenzo et al. | |
| 7,611,671 B2 | 11/2009 | Anvar et al. | |
| 9,304,102 B2 | 4/2016 | Day et al. | |
| 9,518,970 B2 | 12/2016 | Burgi et al. | |
| 9,678,030 B2 | 6/2017 | Potyrailo et al. | |
| 9,759,699 B1 | 9/2017 | Gregory et al. | |
| 10,272,434 B2 | 4/2019 | Khattak et al. | |
| 10,330,624 B2 | 6/2019 | Tayebi et al. | |
| 10,416,140 B2 | 9/2019 | Von Waldkirch | |
| 11,041,838 B2 | 6/2021 | Rogers et al. | |
| 2001/0003249 A1 | 6/2001 | Stormbom | |
| 2004/0241870 A1 | 12/2004 | Miller et al. | |
| 2005/0011260 A1 | 1/2005 | Arndt et al. | |
| 2005/0109621 A1 | 5/2005 | Hauser et al. | |
| 2005/0260453 A1 | 11/2005 | Jiao et al. | |
| 2006/0254501 A1 | 11/2006 | Wang et al. | |
| 2007/0028667 A1 | 2/2007 | Kim et al. | |
| 2007/0045114 A1 | 3/2007 | Wang et al. | |
| 2007/0105341 A1 | 5/2007 | Sosnowchik et al. | |
| 2007/0212263 A1 * | 9/2007 | Shin | G01N 27/16 422/95 |
| 2008/0093226 A1 | 4/2008 | Briman et al. | |
| 2008/0148815 A1 | 6/2008 | Lucas et al. | |
| 2009/0218235 A1 | 9/2009 | McDonald et al. | |
| 2009/0235862 A1 | 9/2009 | Cha et al. | |
| 2009/0249859 A1 | 10/2009 | Takahashi | |
| 2010/0213603 A1 | 8/2010 | Smeys et al. | |
| 2011/0128828 A1 | 6/2011 | Naniwa et al. | |
| 2011/0149465 A1 | 6/2011 | Hashimoto et al. | |
| 2012/0041246 A1 | 2/2012 | Scher et al. | |
| 2012/0192623 A1 | 8/2012 | Adami et al. | |
| 2012/0297860 A1 | 11/2012 | Izawa et al. | |
| 2012/0301360 A1 | 11/2012 | Meinhold et al. | |
| 2014/0036953 A1 | 2/2014 | Kimura et al. | |
| 2014/0208828 A1 | 7/2014 | Von Waldkirch | |
| 2014/0212979 A1 | 7/2014 | Burgi et al. | |
| 2015/0316523 A1 | 11/2015 | Patolsky et al. | |
| 2018/0024089 A1 | 1/2018 | Mickelson et al. | |
| 2018/0031532 A1 | 2/2018 | Lee et al. | |
| 2018/0313800 A1 | 11/2018 | Rogers et al. | |
| 2020/0393432 A1 | 12/2020 | Swanson et al. | |

FOREIGN PATENT DOCUMENTS

| | | |
|---|---|---|
| JP | 2017102131 A | 6/2017 |
| RU | 2709051 C1 | 12/2019 |
| WO | WO-2019083939 A1 | 5/2019 |

OTHER PUBLICATIONS

Banerjee et al., "The Detection of Improvised Nonmilitary Peroxide Based Explosives Using a Titania Nanotube Array Sensor," Nanotechnology, 20—pp. 1-6 (Jan. 2009).

Buttigieg et al. "Characterization of the Explosive Triacetone Triperoxide and Detection by Ion Mobility Spectrometry," Forensic Science International 135:53-59 (Apr. 2003).

Campos et al. "An Electronic Tongue Designed to Detect Ammonium nitrate in Aqueous Solutions," Sensors, 13:14064-14078 (Oct. 2013).

Cho et al., "Colorimetric Sensors for Toxic and Hazardous Gas Detection: A Review," Electronic Materials Letters, 17:1-17 (Published Online Nov. 2020).

Choodum et al., "On-site semi-quantitative analysis for ammonium nitrate detection using digital image colourimetry," Science and Justice, 55:437-445 (May 2015).

Chu, et al., "Detection of Peroxides Using Pd/SnO2(subscript) Nanocomposite Catalysts," Sensors and Actuators B: Chemical, 197:376-384 (Jul. 2014).

Das et al. "Enhanced Response of Co-Planar MEMS Microheater-Based Methane Gas Sensor," IEEE Sensors Journal, 20(23):14132-14140 (Dec. 2020).

De Perre et al. "Rapid and specific detection of urea nitrate and ammonium nitrate by electrospray ionization time-of-flight mass spectrometry using infusion with crown ethers," Rapid Commun. Mass Spectrom., 26:154-162 (2012).

Dong et al., "Simulation of the columnar-to-equiaxed transition in directionally solidified A1-Cu alloys," Acta Materialia, 53:659-668 (2005).

Ewing et al., "A critical review of ion mobility spectrometry for the detection of explosives and explosive related compounds," Talanta, 54:515-529 (2001).

Ewing et al., "Direct Real-Time Detection of RDX Vapors Under Ambient Conditions," Anal. Chem., 85:389-397 (2013).

Ewing et al., "The vapor pressures of explosives," Trends in Analytical Chemistry, 42:35-48 (2013).

Germain et al., "Turn-on Fluorescence Detection of H2O2 and TAPT," Inorganic Chemistry, 47(21):9748-9750 (Nov. 2008).

Gopalakrishnan et al., "Direct Detection of RDX Vapor Using a Conjugated Polymer Network," J. Am. Chem. Soc., 135:8357-8362 (May 2013).

Hampton, M., "Wanted: A Bomb Detector as Sensitive as a Dog's Nose," IEEE Spectrum, Oct. 11, 2019, https://spectrum.ieee.org/tech-talk/semiconductors/devices/using-a-twopronged-approach-to-detect-explosive-substances-from-bombs.

Hsueh et al. "A transparent ZnO nanowire MEMS gas sensor prepared by an ITO microheater," Sensors & Actuators B:Chemical, 304:127319 (Feb. 2020).

Hwang et al., "Development of Micro-Heaters with Optimized Temperature Compensation Design for Gas Sensors," Sensors, 11:2580-2591 (Mar. 2011).

Hwang et al., "Gas sensing properties of SnO2 nanowires on micro-heater," Sensors & Actuators B: Chemical, 154:295-300 (Jun. 2011).

Jung et al., "A low-power embedded poly-Si micro-heater for gas sensor platform based on a FET transducer and its application for NO2 sensing," Sensors & Actuators: B Chemical, 334:129642 (Feb. 2021).

Lee et al., "Highly Sensitive and Multifunctional Tactile Sensor Using Free-standing ZnO/PVDF Thin Film with Graphene Electrodes for Pressure and Temperature Monitoring," Scientific Reports, 5 (7887):1-8 (Jan. 2015).

Lin et al., "A Colorimetric Sensor Array for Detection of Triacetone Triperoxide Vapor," J. Am. Chem. Soc., 132 (44):15519-15521 (Oct. 2010).

Ma et al., "Ultrasensitive, Specific, and Rapid Fluorescence Turn-On Nitrite Sensor Enabled by Precisely Modulated Fluorophore Binding," Adv. Sci., 7:2002991 (1-11), (Nov. 2020).

Malashikhin et al., "Fluorescent Signaling Based on Sulfoxide Profluorophores: Application to the Visual Detection of the Explosive TATP," J. Am. Chem. Soc., 130:12846-12847 (Apr. 2008).

Mallin, Daniel, "Increasing the Selectivity and Sensitivity of Gas Sensors for the Detection of Explosives," Master Thesis, University of Rhode Island (2014).

Moalaghi et al., "Tin oxide gas sensor on tin oxide microheater for high-temperature methane sensing," Material Letters, 263:127196, 4 pages (Mar. 2020).

(56) References Cited

OTHER PUBLICATIONS

Mullen et al.," Laser photoionization of triacetone triperoxide (TATP) by femtosecond and nanosecond laser pulses," International Journal of Mass Spectrometry, 252:69-72 (Feb. 2006).
Mullen et al., "Detection of Explosives and Explosives-Related Compounds by Single Photon Laser Ionization Time-of-Flight mass Spectrometry," Anal. Chem., 78(11):3807-3814 (Jun. 2006).
Rasanen et al., "Determination of gas phase triacetone triperoxide with aspiration ion mobility spectrometry and gas chromatography-mass spectrometry," Analytica Chimica ACTA, 623:59-65 (Jun. 2008).
Ricci et al., "Continuous Monitoring of TATP Using Ultrasensitive, Low-Power Sensors," IEEE Sensors Journal, 20(23):14058-14064 (Dec. 2020).
Ricci et al., "Sensors for the detection of ammonia as a potential biomarker for health screening," Scientific Reports, 11:7185 pp. 1-7 (Mar. 2021).
Ricci et al., "Free-standing, thin-film sensors for the trace detection of explosives," Scientific Reports, 11:6623, 10 pages (Mar. 2021).
Ricci et al., "Orthogonal Sensors for the Trace Detection of Explosives," IEEE Sensors Letters, 3(10):1-4 (Oct. 2019).
Rossi et al., "Trace Detection of Explosives Using Metal Oxide Catalysts," IEEE Sensors Journal, 19(13):4773-4780 (Jul. 2019).
Schulte-Ladbeck et al., "Determination of Peroxide-Based Explosives using Liquid Chromatography with On-Line Infrared Detection," Anal. Chem., 78(23):8150-8155 (Dec. 2006).
Schulte-Ladbeck et al., "Trace Analysis of Peroxide-Based Explosives," Anal. Chem., 75(4):731-735 (Feb. 2003).
Sigman et al., "Analysis of triacetone triperoxide by gas chromatography/mass spectrometry and gas chromatography/tandem mass spectrometry by electron and chemical ionization," Rapid Commun. Mass Spectrom., 20:2851-2857 (Jul. 2006).
Stambouli et al., "Headspace-GC/MS detection of TATP traces in post-explosion debris," Forensic Science International, 146S:S191-S194 (Dec. 2004).
Subramanian et al., "Cu—Pd (Copper-Palladium)," Journal of Phase Equilibria., 12(2):231-243 (1991).
Suematsu et al., "Pulse-Driven Semiconductor Gas Sensors Toward ppt Level Toluene Detection," Anal. Chem., 90:11219-11223 (Aug. 2018).
Sysoev, et al., Percolating SnO2 nanowire network as a stable gas sensor: Direct comparison of long-term performance versus SnO2 nanoparticle films, Sensors and Actuators B, 139(2):699-703 (Jun. 2009).
To et al., "Recent Developments in the Field of Explosive Trace Detection," ACS Nano., 14:10804-10833 (Aug. 2020).
Tong et al., "A fast response and recovery H2S gas sensor based on free-standing TiO2 nanotube array films prepared by one step anodization method," Ceramics International, 43:14200-14209 (Jul. 2017).
Wang et al., "A Colorimetric Artificial Olfactory System for Airborne Improvised Explosive Identification," Adv. Mater., 32(14):1907043, 11 pages (Apr. 2020).
Wang et al., "A MEMS-based Air Flow Sensor with a Free-standing Micro-cantilever Structure," Sensors, 7(10):2389-2401 (Oct. 2007).
Wu et al., "Improved Selectivity and Sensitivity of Gas Sensing Using a 3D Reduced Graphene Oxide Hydrogel with an Integrated Microheater," ACS App. Mater. Interfaces, 7(49):27502-27510 (Dec. 2015).
Xu et al., "Surface Plasmon Resonances of Free-Standing Gold Nanowires Fabricated by Nanoskiving," Angew. Chem. Int. Ed., 45(22):3631-3635 (May 2006).

* cited by examiner

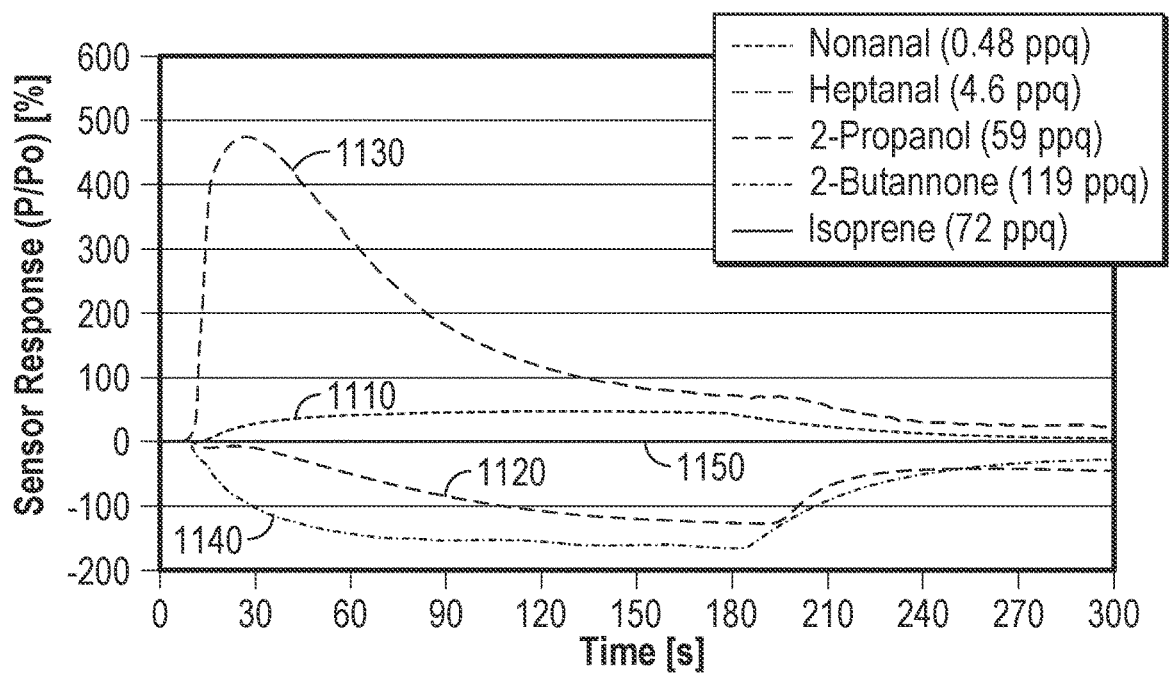
FIG. 11
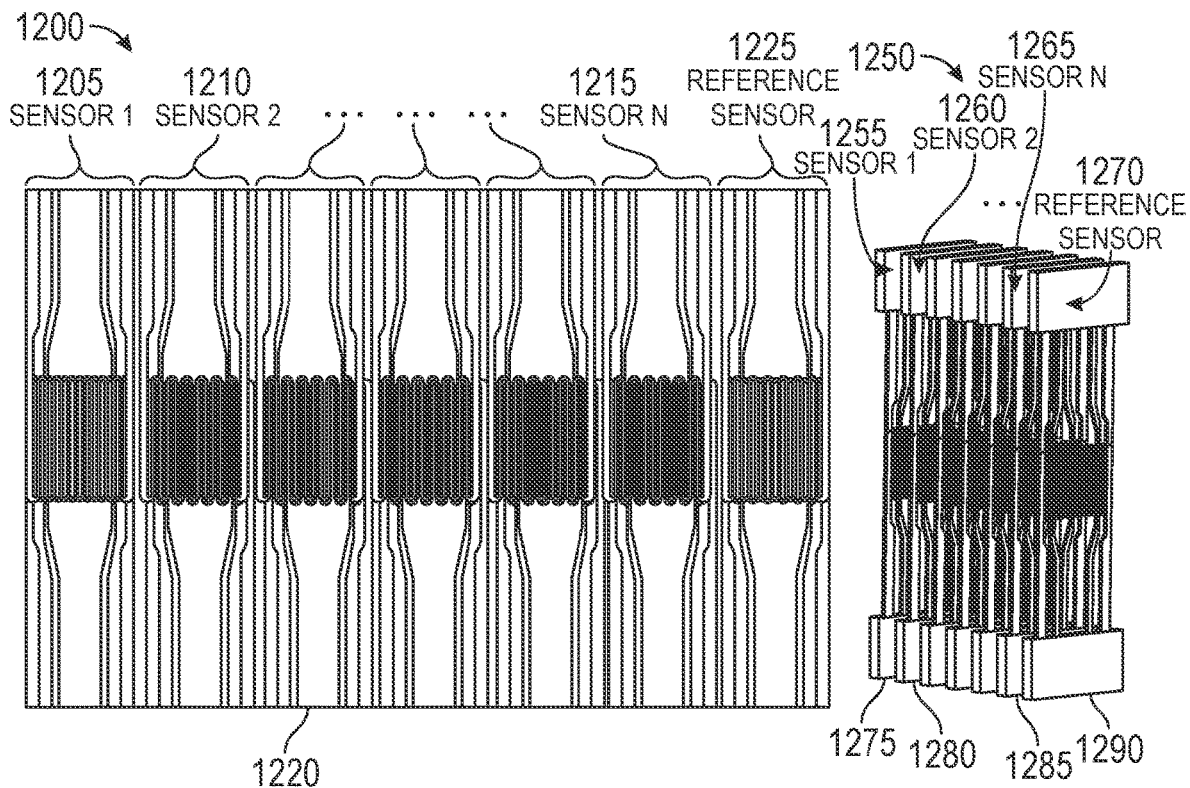
FIG. 12A
FIG. 12B

1300

Legend:
- + Positive Response (Endothermic)
- − Negative Response (Exothermic)
- NR No Response

| | $Al_2CuO_4$ | $Fe_2O_3$ | ITO | MnO | SnO | WO |
|---|---|---|---|---|---|---|
| Optimal Operating Temperature (°C) | 250 | 175 | 175 | 250 | 175 | 250 |
| Acetone (10ppm) | − | − | + | − | + | − |
| AN (14ppb) | + | NR | + | + | + | NR |
| RDX (7ppt) | + | NR | + | NR | + | NR |
| $H_2O_2$ (7ppm) | + | − | − | + | − | + |
| TATP (20ppm) | NR | NR | + | NR | + | NR |
| DADP (50ppm) | − | NR | − | − | + | NR |
| 2,4-DNT (0.18ppm) | + | NR | + | + | + | + |
| CBD (13ppt) | NR | + | + | NR | + | + |
| THC (0.15ppt) | − | − | − | NR | + | + |
| Glucose (80ppq) | + | NR | + | NR | + | − |
| Fructose (15ppt) | + | NR | − | − | + | NR |
| Ammonia (7ppm) | + | − | + | + | + | − |
| Natural Gas (7ppm) | + | − | + | + | + | + |
| Methanol (15ppm) | + | − | + | + | + | + |

Legend:
- + Positive Response (Endothermic)
- − Negative Response (Exothermic)
- NR No Response

| | $Al_2CuO_4$ | CuO | $Fe_2O_3$ | ITO | MnO | SnO | WO |
|---|---|---|---|---|---|---|---|
| Optimal Operating Temperature (°C) | 250 | 250 | 175 | 175 | 250 | 175 | 250 |
| Acetone (10ppm) | − | − | − | + | − | + | − |
| Glucose (80ppq) | + | − | NR | + | NR | + | − |
| Fructose (15ppt) | + | NR | NR | − | − | + | NR |
| Ammonia (7ppm) | + | − | − | + | + | + | − |
| $H_2O_2$ (7ppm) | + | − | + | − | + | − | + |
| Nonanal (0.48ppq) | + | − | NR | + | NR | + | + |
| Heptanal (4.6ppq) | NR | − | − | + | − | + | + |
| Ethylbenzene (12ppq) | − | NR | − | − | − | + | − |
| 2-propanol (59ppq) | − | − | − | + | − | + | + |
| 2-Butanone (119ppq) | + | − | − | − | − | + | − |
| Isoprene (72ppq) | + | − | NR | + | NR | + | NR |

FIG. 14

DECOUPLED THERMODYNAMIC SENSING SYSTEM

CROSS-REFERENCE TO RELATED APPLICATIONS

This application claims the benefit of U.S. Provisional Patent Application No. 63/110,829, filed Nov. 6, 2020 and titled "Decoupled Thermodynamic Sensing System," the entire contents of which are incorporated by reference herein.

TECHNICAL FIELD

The present disclosure describes an ultrasensitive, ultrathin thermodynamic sensing platform for the detection of chemical compounds in the vapor phase at the single molecule level. This thermodynamic sensor platform may be referred to herein as a "decoupled thermodynamic sensor." The sensing system described within decouples the heating and sensing functions, resulting in unparalleled sensor selectivity and sensitivity at the single molecule level. The decoupled thermodynamic sensor described within has been used to detect chemical compounds, including explosives (including triacetone triperoxide (TATP) and dinitrotoluene (DNT)), narcotics and drugs (including fentanyl and cocaine), hallucinogenic and non-hallucinogenic compounds (including cannabidiol (CBD) and tetrahydrocannabinol (THC)), and a variety of other VOCs (acetone, natural gas, propane, etc.). The sensing system is especially designed for a variety of healthcare applications including breathalyzers and wearables. The decoupled thermodynamic sensing system has been used to detect breath, skin, and sweat biomarkers related to variety of chronic and acute diseases (including diabetes, chronic kidney disease (CKD), Alzheimer's, and cancer).

BACKGROUND

Sensors utilizing microheaters have been shown to be effective in detecting explosives, such as triacetone triperoxide (TATP), in the vapor phase at trace levels. Such sensors include those described in U.S. Pat. No. 9,759,699 to Gregory et al. and Ricci et al., "Continuous Monitoring of TATP Using Ultrasensitive, Low-Power Sensors," published on 9 Jul. 2020 in IEEE Sensors Journal, the entire contents of each of which are incorporated herein by reference. While those sensors are extremely effective, it is desirable to provide sensors having increased sensitivity.

Those existing chemical sensors comprise relatively thick (measured in hundreds of micrometers) alumina substrates, relatively thick nickel films for the microheaters, and a thick passivation layer between the heater and the catalyst. Additionally, a temperature of approximately 500° C. is required to operate these sensors, and therefore a significant amount of power is required for the heaters. The relatively large thermal mass of the components of these sensors further adds to the required power to operate. Additionally, these sensors contained a substrate that was isotropic, which transferred heat in all directions. This large thermal mass in combination with the lateral heat transfer was found to affect the accuracy of the heat measurements of the catalyst.

Other known sensors attempted to reduce the thermal mass. For example, similar sensors were manufactured using ultrathin (<50 μm) substrates. Such sensors demonstrated lower operating temperature requirements, improved sensor response time, and improved sensitivity. Nevertheless, these sensors still required a temperature of 175° C. to operate and had detection limits at the part-per-trillion (ppt) level.

In view of the foregoing drawbacks of previously known systems, there exists a need for chemical sensors that operate at less than 175° C.

It further would be desirable to have chemical sensors that require less power to operate than some known systems.

It further would be desirable to have chemical sensors that are capable of detection of substances in extremely low concentrations.

SUMMARY

Provided herein is a decoupled thermodynamic sensing system with unparalleled sensitivity. As used herein, a thermodynamic sensing system is "decoupled" if a heating device of the system is separate from and not in contact with a thin-film sensor in the system. An example of a decoupled detection device includes one in which a substrate is disposed between a microheater and a thin-film sensor. Embodiments of a decoupled sensor can operate at temperatures much lower than 175° C. and use considerably less power than known sensors. Moreover, embodiments of a thermodynamic sensing system in accordance with the present invention have decoupled heating and sensing layers resulting in improved sensitivity and are capable of single molecule detection, i.e. detecting a single molecule of a chemical compounds in the vapor phase.

In some preferred embodiments, the sensor comprises a copper-based microheater deposited onto ultrathin (<40 μm thick) yttria-stabilized-zirconia substrates, which results in improved heating efficiency due to the electrical and thermal conductivity of the copper. Moreover, in preferred embodiments, the sensor comprises a palladium-based microheater deposited onto the opposite face of the ultrathin yttria-stabilized-zirconia substrates, which results in increased sensor sensitivity and selectivity over known devices. Embodiments of a decoupled thermodynamic sensor display highly anisotropic thermal characteristics, which results in localized heating between substrate surfaces. Embodiments of a decoupled thermodynamic sensor require that the microheaters be precisely aligned as such to guarantee optimal heating efficiency with corresponding improvements to the power efficiency. Embodiments of a decoupled thermodynamic sensor have displayed the ability to detect one or more chemical compounds in the vapor phase at the single molecule level with relatively minimal power requirements.

In accordance with some aspects, a detection device is provided that includes at least one multi-layer sensor. In some embodiments, the sensor(s) has four layers. For example, the sensor may include a first layer having a microheater (e.g., a metallic microheater) configured to receive power at a first power level to reach a setpoint temperature, a second layer in contact with the first layer, a third layer in contact with the second layer, and a fourth layer in contact with the third layer. The second layer may be a substrate. The third layer may be a thin-film metallic sensor configured to measure the power level resulting from heat effects due to chemical reactions. The fourth layer may include a catalyst configured to undergo a chemical reaction when exposed to an analyte. The chemical reaction may be endothermic or exothermic. The metallic microheater may receive power at a first power level to maintain a setpoint temperature and provide heat to the metallic sensor. The metallic sensor may receive power at a second power level to measure the response after the catalyst begins the chemical reaction.

In some embodiments, the metallic microheater may be copper. The substrate may be yttria-stabilized-zirconia. The thin-film sensor may be palladium. The catalyst may be a metal oxide catalyst. The substrate may have a thickness of less than 40 micrometers.

The detection device may detect the analyte in a vapor phase based on the heat effect. The detection device may detect the analyte at concentration levels as low as a single molecule level.

The detection device may include a controller configured to cause the power to be provided to the metallic microheater at the first power level to reach the setpoint temperature, to cause the power to be provided to the metallic sensor at the second power level to maintain the setpoint temperature after the catalyst begins the chemical reaction, and determine an existence, identity, and/or concentration of the analyte based on monitoring the second power level. As will be readily understood, the detection device may determine the existence, identity, and/or concentration of one or more additional analytes as well.

The detection device may include a reference sensor that is not coated with a catalyst. The detection device may include a second decoupled sensor having a second microheater and a second thin-film sensor in thermal communication with a second catalyst different from the first catalyst. The detection device may include third, fourth, and fifth sensors comprising third, fourth, and fifth catalysts, respectively.

In some embodiments, the first catalyst comprises aluminum copper oxide ($Al_2CuO_4$), the second catalyst comprises iron oxide ($Fe_2O_3$), the third catalyst comprises indium-tin oxide (ITO), the fourth catalyst comprises tin oxide (SnO), and the fifth catalyst comprises tungsten oxide (WO). The detection device may include a sixth sensor comprising a sixth catalyst selected from copper oxide (CuO) or manganese oxide (MnO).

In accordance with some aspects, a detection device is provided with an array of sensors that are electrically coupled to a controller. Each sensor in the array may have its own distinct catalyst such that reactions between an analyte(s) and the distinct catalysts (to the extent a reaction occurs) indicate information on the existence, identity, and/or concentration of the analyte(s). For example, the reactions may be thermal, and the controller may monitor the variations in power applied to each sensor to determine the existence, identity, and/or concentration of the analyte(s). Each of the sensors in the array may be formed from the multi-layer configuration described above with its own distinct catalyst. A reference sensor may be included in the array that is formed in the multi-layer manner, but without a catalyst.

In some embodiments, a first decoupled sensor has a first microheater, a first metallic sensor, and a first catalyst in thermal communication with the first metallic sensor, and a second decoupled sensor has a second microheater layer, a second metallic sensor layer and a second catalyst layer in thermal communication with the second metallic sensor layer. The controller may be in electrical communication with the first decoupled sensor and the second decoupled sensor. The controller may cause power to be provided to the first and second decoupled sensors to heat the first microheater to a first setpoint temperature and to heat the second microheater to a second setpoint temperature, vary power applied to the first sensor and/or the second sensor to account for a thermal response caused by reactions between an analyte and the first catalyst layer and/or the second catalyst layer to maintain the first setpoint temperature and the second setpoint temperature, and determine an existence, identity, and/or concentration of the analyte based on the varied the power. The first setpoint temperature may be the same temperature as the second setpoint temperature.

In some embodiments, the detection device includes a reference sensor having a reference microheater and without a catalyst, the reference sensor in electrical communication with the controller. The detection device may include a third decoupled sensor comprising a third microheater, a third metallic sensor and a third catalyst in thermal communication with the third metallic sensor, a fourth decoupled sensor comprising a fourth microheater, a fourth metallic sensor, and a fourth catalyst in thermal communication with the fourth metallic sensor, and a fifth decoupled sensor comprising a fifth microheater, a fifth metallic sensor and a fifth catalyst in thermal communication with the fifth metallic sensor. In some embodiments, the first catalyst comprises aluminum copper oxide ($Al_2CuO_4$), the second catalyst comprises iron oxide ($Fe_2O_3$), the third catalyst comprises indium-tin oxide (ITO), the fourth catalyst comprises tin oxide (SnO), and the fifth catalyst comprises tungsten oxide (WO). The detection device may include a sixth sensor comprising a sixth catalyst selected from copper oxide (CuO) or manganese oxide (MnO). As will be readily understood, the detection device may include more than six decoupled sensors and each additional decoupled sensor preferably has its their own distinct catalyst.

In some embodiments, the first catalyst, the second catalyst, the third catalyst, the fourth catalyst, and the fifth catalyst each comprise aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), or tin oxide (SnO). The setpoint temperature may be between 30° C. and 500° C.

In accordance with some aspects, a method of detecting an analyte is provided. The method may include providing a decoupled sensor array comprising a first decoupled sensor and a second decoupled sensor, the first decoupled sensor comprising a first microheater layer, a first sensor layer and a first catalyst layer in thermal communication with the first sensor layer, the second decoupled sensor comprising a second microheater layer, a second sensor layer and a second catalyst layer in thermal communication with the second sensor layer; delivering power to the first and second microheaters to heat the first sensor to a first setpoint temperature and to heat the second sensor to a second setpoint temperature; exposing the first and second sensors to an analyte such that the first catalyst layer and/or the second catalyst layer react with the analyte to generate a thermal response; varying power applied to the first sensor and/or the second sensor to account for the thermal response to maintain the first setpoint temperature and the second setpoint temperature; and/or determining an existence, identity, and/or concentration of the analyte based on varying the power.

Determining the existence, identity, and/or concentration of the analyte based on varying the power may include comparing the thermal response to a database of known thermal responses. The sensor array may include a reference sensor and determining the existence, identity, and/or concentration of the analyte may include analyzing information on power supplied to the reference sensor. In some embodiments, the first catalyst layer comprises aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), or tin oxide (SnO). In some embodiments, the second catalyst layer comprises aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), or tin oxide (SnO).

The detection device described herein may be used to detect a variety of analytes including but not limited to explosives (including triacetone triperoxide (TATP) and dinitrotoluene (DNT)), narcotics and drugs (including fentanyl and cocaine), hallucinogenic and non-hallucinogenic compounds (including cannabidiol (CBD) and tetrahydrocannabinol (THC)), and a variety of other VOCs (acetone, natural gas, propane, etc.). The sensing system is especially designed for a variety of healthcare applications including breathalyzers and wearables. The decoupled thermodynamic sensing system has been used to detect breath, skin, and sweat biomarkers related to a variety of chronic and acute diseases (including diabetes, chronic kidney disease (CKD), Alzheimer's, and cancer).

BRIEF DESCRIPTION OF THE DRAWINGS

FIG. 11 shows an illustrative graphical representation of a comparison between responses of a decoupled thermodynamic ultrathin vapor sensor employing an WO catalyst to variety of analytes of different vapor pressures at an operating temperature of 250° C.

FIGS. 12A and 12B depict embodiments of sensor arrays in which the substrate is shared by the sensors and in which each sensor has an individual substrate, respectively.

FIG. 13 shows a summary table consisting of the thermodynamic sign indicative of the measured redox reactions, for six catalysts making up a decoupled thermodynamic sensor array.

FIG. 14 shows a summary table consisting of the thermodynamic sign indicative of the measured redox reactions, for six catalysts making up a decoupled thermodynamic sensor array.

DETAILED DESCRIPTION OF THE PREFERRED EMBODIMENTS

Figure 1A:
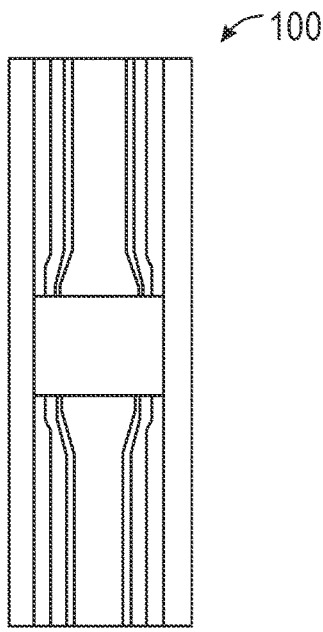
FIG. 1A shows an illustrative diagrammatic view of the top of a sensor in accordance with an embodiment of the present invention.

Described herein is the decoupled thermodynamic sensing system utilizing decoupled heating and sensing resistors. Embodiments of the present invention are capable of single molecule detection (of compounds in the gas phase). Embodiments of the decoupled thermodynamic sensors comprise at least two sensors, one or more catalyst coated "active" sensors and an uncoated "reference" sensor. The microheaters preferably are thermally scanned over a selected temperature range and electrically powered, and preferably are configured to maintain a constant temperature. Heat is transferred from the microheater layer (on one face of the substrate) to the sensor layer (on the opposite face of the substrate). After reaching a set temperature and establishing equilibrium, a relatively low amount of electrical power may be provided to the sensor to enable measurement. The power difference between the reference (uncoated) sensor layer and a catalyst-coated sensor layer may be measured. This electrical power difference is the heat effect associated with oxidation/reduction reactions that occur on the surface of the catalyst after decomposition of a target molecule has occurred.

Measurement of the power difference between a sensor and the reference may be obtained utilizing a controller integrating Wheatstone bridge circuitry, or more preferably a half-Wheatstone bridge or an Anderson loop for increased efficiency. It will be appreciated that changes in the electrical power of the reference microheater and the catalyst coated microheater may be used to calculate the power difference and thus, the response of the sensor platform.

In operation of embodiments, the reference (uncoated) microheater and the catalyst coated microheaters are electrically powered to a predetermined setpoint temperature.

Heat is transferred from the microheater (on one face of the substrate) to the thin-film sensor (on the opposite face of the substrate) until equilibrium is established at the setpoint temperature. After raising the microheater to the setpoint temperature, a relatively low amount of electrical power is then provided to the thin-film sensor to enable measurement. Upon introduction of the analyte, the vapor sensor system qualitatively or quantitatively measures the heat effect associated with interactions between the catalyst(s) and the analyte. In general, oxidation reactions release heat, resulting in less electrical power required to maintain the same temperature and are therefore associated with negative responses. Conversely, reduction reactions absorb heat requiring more electrical power to maintain the same temperature and are therefore associated with positive responses. These heat effects are the result of oxidation/reduction reactions on the catalyst surface and the catalytic decomposition of the target molecule. The reference sensor is used to monitor sensible heat effects and other hydrodynamic effects, thus, mitigating false positives/negatives. As a result, the heat effect may be quantified, as well as qualified as endothermic, exothermic, or neither. Different catalysts used in different sensors in the detection system may experience a different heat effect when exposed to the same analyte. By comparing the quantitative or qualitative results from a plurality of sensors of a system to known results, the existence and concentration of an analyte may be determined.

The detection system described herein may be used to detect chemical compounds, including explosives (including triacetone triperoxide (TATP) and dinitrotoluene (DNT)), narcotics and drugs (including fentanyl and cocaine), hallucinogenic and non-hallucinogenic compounds (including cannabidiol (CBD) and tetrahydrocannabinol (THC)), and a variety of other VOCs (acetone, natural gas, propane, etc.). The sensing system is especially designed for a variety of healthcare applications including breathalyzers and wearables. The decoupled thermodynamic sensing system has been used to detect breath, skin, and sweat biomarkers related to variety of chronic and acute diseases (including diabetes, chronic kidney disease (CKD), Alzheimer's, and cancer).

Experiments employing aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), and tin oxide (SnO) catalysts were performed. As a result of experiments using sensors comprising ultrathin YSZ ceramic substrates, the sensing mechanism was confirmed for a number of these analytes.

The present disclosure is an ultrasensitive chemical (vapor) sensing platform, whereby the heating and sensing functions of the sensor platform are decoupled, relative to other thermodynamic sensing platforms, where thin film microheaters serve both purposes or heating and sensing. This decoupling was accomplished by utilizing two different thin-film resistors with one resistor being a heater and the other being a sensor. These resistors were deposited onto opposite faces of an ultrathin yttria-stabilized-zirconia (YSZ) substrate (having a thickness of less than 50 μm). Using this ultrasensitive chemical sensing platform has advantageously resulted in detection of a single molecule of vapor phase compounds, which demonstrates greater sensitivity over other systems. In some embodiments, this sensing platform includes two different thin-film resistors which are deposited in such a way that they are aligned to one another on opposite faces of an ultrathin YSZ substrate. One thin film microheater (resistor) was deposited on the back of the substrate and is electrically powered to maintain a predetermined setpoint temperature. Another thin-film sensor (resistor) is aligned to and deposited onto the opposite face of the substrate and is coated with a metal oxide catalyst. Upon reaching the desired temperature, the thin film sensor (thin film resistor) is "activated" using a small trickle current to measure the voltage. Here, the heat generated by the microheater on the opposite face of the YSZ is used to heat the sensor to the same setpoint temperature while maintaining minimal power level for operation. Other thermodynamic sensing platforms have shown that a reduction in thermal mass yields improved sensitivity and response times at drastically lower operating temperatures. However, these sensors rely on a single thin film microheater to reach and maintain the desired temperature setpoint as well as detect the target molecules resulting in relatively large operating powers (e.g., greater than 400 mW). By decoupling the heating and sensing functionalities utilizing two different thin film resistors deposited on opposite sides of the ultrathin YSZ substrate, these power draws were significantly reduced. Utilizing a separate microheater on opposite faces of the substrate, the sensor can reach the desired operating temperature (e.g., below 200° C.) at a low lower level (e.g., less than 3 mW).

Figure 1B:
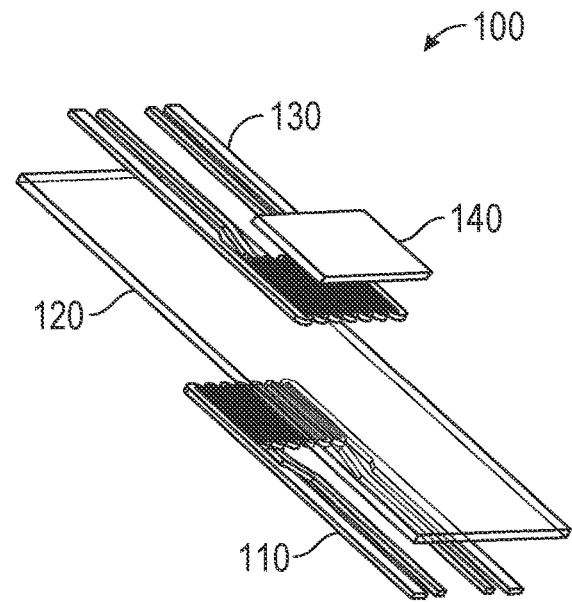
FIG. 1B shows an illustrative diagrammatic view of the sensor in accordance with an embodiment of the present invention, showing the expanded view of the catalyst layer, sensing layer, ultrathin substrate, and microheater layer.

FIG. 1A and FIG. 1B show a top view of decoupled thermodynamic sensing platform 100 and a cross-sectional view of decoupled thermodynamic sensing platform 100, respectively. As illustrated in FIG. 1B, detection device 100 may include multiple layers, such as microheater layer 110, substrate layer 120, thin-film sensor layer 130, and catalyst layer 140.

Microheater layer 110, a resistor, may be formed of metal. Microheater layer 110 is designed to maintain a setpoint temperature. In some embodiments, microheater 110 is formed using photolithography to pattern a 1-micrometer thick film of copper, which has considerably lower thermal mass than free-standing 25-micrometer diameter nickel wires used in other known sensors. Copper is the preferred choice for the metallization due to its high electrical conductivity and thus, low power and voltage requirements. However, any conductive metal can be used including silver and gold.

In preferred embodiments, substrate 120 is an ultrathin YSZ substrate, which comprises a nominal thickness (e.g., 20 micrometers). Ultrathin YSZ substrates that display a selected temperature difference (e.g., less than 1° C. temperature difference) between the front and back of the substrate, due to its thickness anisotropy are preferred. Thus, the heat generated from the back microheater remains in the vicinity of catalyst on the opposite face, allowing for uniform heating of the sensor without dissipating throughout the rest of the sensor platform. Notably, layers of the decoupled thermodynamic sensor may have different thicknesses, and the films may be optimized for thickness to maximize surface area of the metal oxide catalyst while still maintaining the low mass characteristics of the microheater.

Thin-film sensor layer 130 may be formed of metal. Sensor layer 130 is designed to measure power changes via the addition or reduction of heat upon exposure to an endothermic or exothermic chemical reaction, respectively, at catalyst layer 140. In some embodiments, thin-film sensor 130 is formed using photolithography to pattern a 1-micrometer thick palladium film microheater. Palladium is a preferred choice for the metallization due to its catalytic amplification effect, which has been shown to improve sensitivity and response time.

Catalyst layer 140 is coated with a catalyst selected for detection of a predetermined analyte. The catalyst may be selected to chemically react with the analyte selected for detection.

Figure 1C:
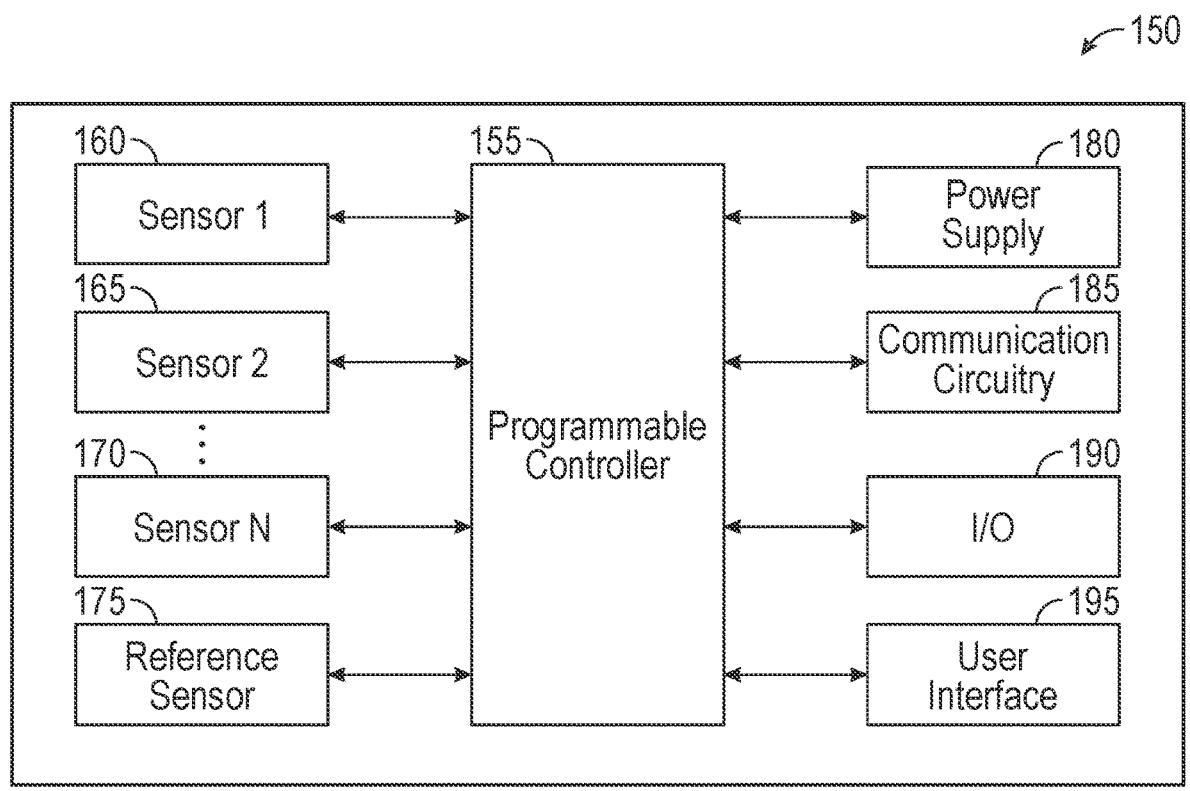
FIG. 1C shows a schematic diagram of an exemplary detection device.

FIG. 1C illustrates a generalized schematic diagram of the internal functional components of an exemplary detection device. Detection device 150 includes a plurality of sensors in communication with programmable controller 155. The plurality of sensors includes first sensor 160, second sensor 165, and so forth up to and including Nth sensor 170. Each of sensors 160, 165, 170 may be constructed in the manner described for the sensor in FIGS. 1A and 1B, although in some embodiments, each sensor has a different catalyst. Sensors also may include reference sensor 175, which may be constructed in the manner described for the sensor in FIGS. 1A and 1B, although the reference sensor preferably does not include a catalyst. Programmable controller 155 is in electronic communication with each of the plurality of sensors. Specifically, programmable controller 155 may provide a known amount of power to each of the plurality of sensors, though it will be appreciated that in some uses not all of the sensors will be necessary and in such cases programmable controller 155 may selectively provide power to the subset of the sensors that are necessary. Programmable controller 155 is configured to determine the amount of power provided to each of the sensors and to compare the power provided to any individual sensor (e.g., Nth sensor 170) to the power provided to reference sensor 175. Programmable controller 155 may integrate Wheatstone bride circuitry for each sensor, or more preferably a half-Wheatstone bridge or an Anderson loop for increased efficiency.

Detection device 150 further includes power supply 180, communication circuitry 185, input/output 190 and user interface 195, each of which are coupled to controller 155.

User interface 195 may be used to receive inputs from, and provide outputs to, a user. For example, user interface 195 may provide information to the user on the existence, identity, and/or concentration of an analyte detected by detection device 150. User interface 195 may include a power switch that completes a circuit between power supply 180 and controller 155 to selectively activate an operational mode of device 155. User interface 195 may include a setpoint temperature controller, wherein the user may select one or more operating temperatures for the plurality of sensors. User interface 195 may further include a volume control to selectively increase or decrease an audio output.

User interface 195 may include a touchscreen, switches, dials, lights, an LED matrix, other LED indicators, or other input/output devices for receiving inputs from, and providing outputs to, a user. In other embodiments, user interface 195 is not present on detection device 150, but is instead provided on a remote computing device communicatively connected to detection device 150 via the communication circuitry 185. User interface also may be a combination of elements on the detection device and a remote computing device.

Input and output circuitry (I/O) 190 may include ports for data communication such as wired communication with a computer and/or ports for receiving removable memory, e.g., SD card, upon which program instructions or data related to known reactions may be stored and/or for transmitting power to detection device 150. In one embodiment, I/O 190 comprises ports, and corresponding circuitry, for accepting cables such that controller 155 is electrically coupled to an externally located computer system.

Power supply 180 may supply alternating current or direct current. In direct current embodiments, power supply may include a suitable battery, such as a replaceable battery or rechargeable battery, and apparatus may include circuitry for charging the rechargeable battery, and a detachable power cord. Power supply 180 may be charged by a charger via an inductive coil within the charger and inductive coil. Alternatively, power supply 180 may be a port to allow device 150 to be plugged into a conventional wall socket, e.g., via a cord with an AC to DC power converter, for powering components within the device. Power supply 180 may be designed to supply power to the components of detection device 150. For example, power supply 180 may, responsive to instructions by controller 155, supply power to each of the sensors to maintain a setpoint temperature(s) and to vary the power supplied to each of the sensors to maintain the setpoint temperature(s) as the respective catalysts undergo thermal reactions with an analyte (if present).

Controller 155 includes electrical components and permits electrical coupling between controller 155 and sensors (e.g., first sensor 160, second sensor 165, N additional sensors 170, reference sensor 175) and other components, when included, such as communication circuitry 185, input/output 190, and user interface 195. Controller includes memory, which may be RAM, ROM, Flash, or other known memory, or some combination thereof. Controller preferably includes storage in which data may be selectively saved. For example, programmable instructions may be stored to execute algorithms for detecting the existence, identity, and/or concentration of an analyte based on the amount of power the controller causes to be supplied to each of the sensors in the array. The instructions may utilize information stored (e.g., in lookup tables) to determine information on the analyte. One or more electrical components and/or circuits may perform some of or all the roles of the various components described herein. Although described separately, it is to be appreciated that electrical components need not be separate structural elements. For example, controller 155 and communication circuitry 185 may be embodied in a single chip. In addition, while controller 155 is described as having memory, a memory chip(s) may be separately provided.

Controller 155 may be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. A controller may also be implemented as a combination of computing devices, e.g., a combination of a DSP and a microprocessor, a plurality of microprocessors, one or more microprocessors in conjunction with a DSP core, or any other such configuration.

Controller 155 may contain memory and/or be coupled, via one or more buses, to read information from, or write information to, memory. The memory may include processor cache, including a multi-level hierarchical cache in which different levels have different capacities and access speeds. The memory may also include random access memory (RAM), other volatile storage devices, or non-volatile storage devices. The storage devices can include, for example, hard drives, optical discs, flash memory, and Zip drives.

Controller 155, in conjunction with firmware/software stored in the memory may execute an operating system, such as, for example, Windows®, Mac OS®, Unix® or Solaris® 5.10. Controller 155 also executes software applications stored in the memory. In one non-limiting embodiment, the software comprises, for example, Unix® Korn shell scripts. In other embodiments, the software may be programs in any suitable programming language known to those skilled in the art, including, for example, C++®, PHP®, or Java®.

Communication circuitry 185 is configured to transmit information, such as signals indicative of the presence, absence, and/or quantity of one or more target analytes, locally and/or to a remote location such as a server. Communication circuitry 185 is configured for wired and/or wireless communication over a network, such as the Internet, a telephone network, a Bluetooth® network, and/or a WiFi network, using techniques known in the art. Communication circuitry 185 may be a communication chip known in the art, such as a Bluetooth® chip and/or a WiFi chip. Communication circuitry 185 may include a receiver and a transmitter, or a transceiver, for wirelessly receiving data from, and transmitting data to a remote computing device. In some such embodiments, the remote computing device may be a mobile computing device that provides the system with a user interface; additionally, or alternatively, the remote computing device is a server. In embodiments configured for wireless communication with other devices, communication circuitry 185 may prepare data generated by controller 155 for transmission over a communication network according to one or more network standards and/or demodulates data received over a communication network according to one or more network standards.

In operation, the decoupled thermodynamic sensing system may be exposed to an analyte, such as a chemical compound. Upon exposure to the analyte, catalyst 140 may undergo a chemical reaction with the analyte, which may be an endothermic or exothermic reaction. If thin-film sensor 130 experiences any temperature change from the chemical reaction, there may be an associated demand for increased power to maintain the setpoint temperature in response to an endothermic reaction or a demand for less power to maintain the setpoint temperature in response to an exothermic reaction. This demand occurs at a rate related to the temperature change caused by the chemical reaction with the analyte to which the detection device has been exposed. The power provided to thin-film sensor 130 is minimal due to the effects of the heat transfer provided by microheater layer 110.

Figure 2:
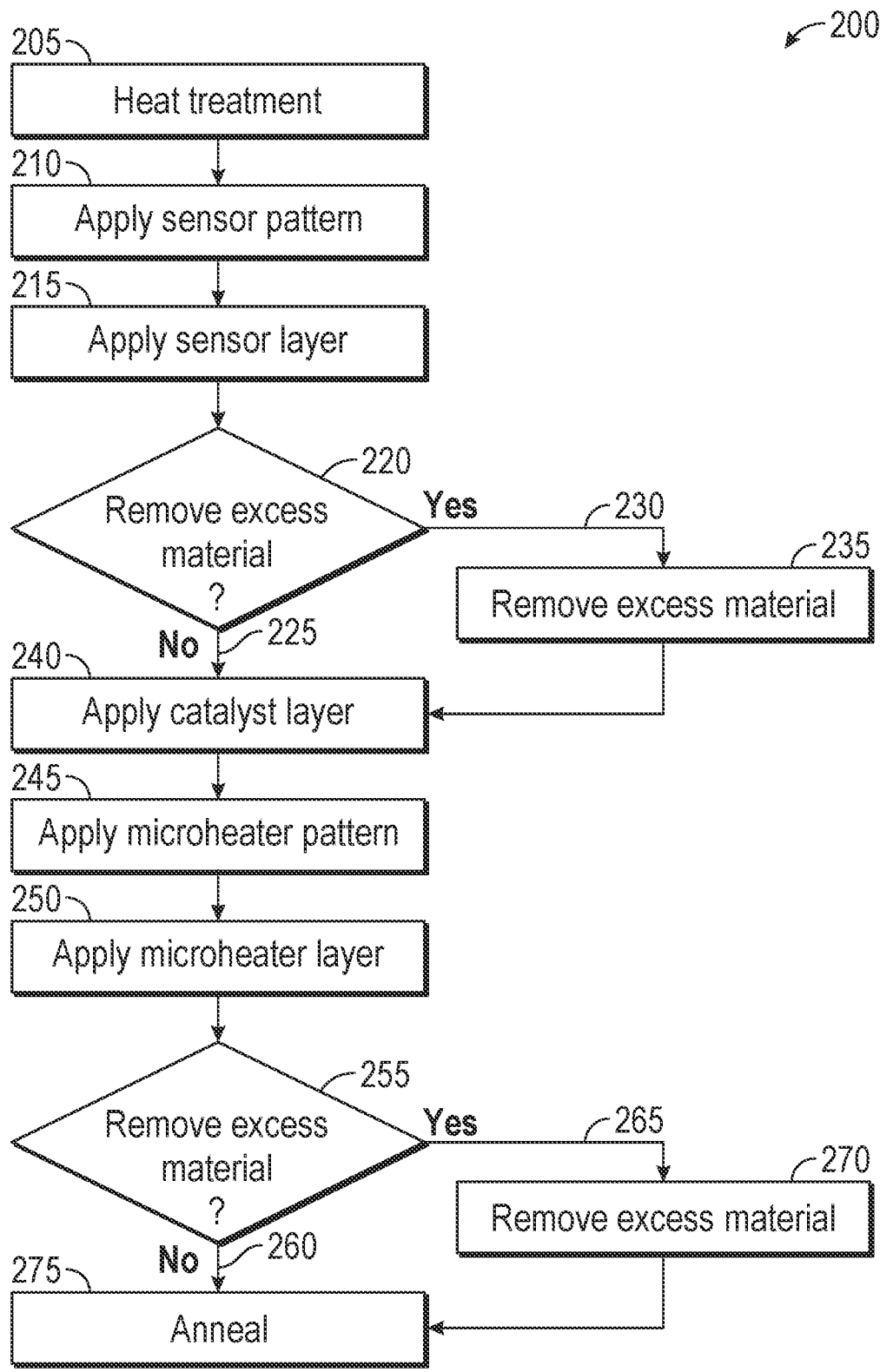
FIG. 2 shows a flowchart describing an exemplary fabrication procedure of a decoupled thermodynamic sensor.

Exemplary method 200 of forming a decoupled thermodynamic sensor in accordance with the present invention is illustrated in FIG. 2. The heat treatment step 205 involves heat treating a substrate. In preferred embodiments, the substrate is a YSZ substrate, and the heat treatment occurs in ambient air at an elevated temperature (e.g., 1000° C.) over a period of time (e.g., three hours). At step 210, a sensor pattern is applied to the substrate. The pattern is preferably applied using photolithography or shadow masking, but it will be appreciated that other known techniques may be utilized. In preferred embodiments, the pattern includes a serpentine region in which portions of the pattern's path may remain close to other portions of the pattern's path. The serpentine region may be sinusoidal, zigzag, irregular, a series of straight or curved segments, or other configuration that may be desired based on heat transfer characteristics, aesthetics, or other desirable characteristics. The sensor layer is applied at step 215. The sensor layer may be applied using sputtering, evaporation, or other known techniques. Step 220 provides an optional decision as to whether it is desirable to remove excess material. If it is not desired, the method proceeds along path 225 to step 240. If it is desirable to remove excess material, such as if photolithography is utilized, then the method proceeds along path 230 to step 235, which involves removal of the extra material. In some embodiments, optional step 235 involves lifting off excess palladium metallization, leaving the remaining palladium-based sensor adhered to the YSZ substrate before continuing to step 240. At step 240 the catalyst layer is applied. In some preferred embodiments, a metal oxide catalyst is applied in a layer having a thickness (e.g., 1.2 micrometers) over the serpentine region of the palladium sensor. Proceeding to step 245, a microheater pattern is applied to the substrate, preferably in region opposite the face of the substrate on which the sensor is located. Following the application of the microheater pattern, the microheater layer is applied at step 250. The microheater layer may comprise copper that is applied using sputtering, evaporation, or other known techniques, but the microlayer additionally or alternatively may comprise other materials. It will be appreciated that applying the microheater and thin-film sensor to opposite sides of the substrate results in decoupling of the microheater and sensor, which are further separated by the substrate layer. Step 255 provides an optional decision as to whether it is desirable to remove excess material from the microheater layer. If it is not desired, the method proceeds along path 260 to step 275. If it is desirable to remove excess material, such as if photolithography is utilized, then the method proceeds along path 265 to step 270, where the extra material is removed. In some embodiments, optional step 270 involves lifting off excess copper metallization, leaving the remaining microheater layer adhered to the YSZ substrate. Annealing is performed at step 275. In preferred embodiments, the copper-based microheater and palladium-based sensor are annealed at a temperature (e.g., 500° C.) for a period of time (e.g., 30 minutes) in a nitrogen atmosphere. It will be appreciated that steps for forming the sensor are limited to the order of method 200. For example, in some methods, the microheater may be applied to the substrate before the application of the sensor.

In developing embodiments of decoupled thermodynamic sensors in accordance with the present invention, a number of problems were identified and overcome. For example, YSZ substrates displayed increasing electrical conductivity at higher temperatures. This property promoted electrical shorting between a copper-based microheater and a palladium-based sensor. This electrical short was mitigated via precise alignment of the microheater and sensor serpentines. By avoiding any potential electrical contact between the two films, the microheater was able to reach the desire temperature setpoint by transferring any current or voltage to the sensor resistor. Advantageously, and unlike known thermodynamic sensing platforms, the decoupled thermodynamic sensor does not require an aluminum oxide passivation layer between the catalyst and the sensor resistor. Removal of this layer further reduced the thermal mass by orders of magnitude relative to the alumina coatings employed in previous solid-state sensors which comprised an alumina cement layer with a thickness on the order of hundreds of micrometers. The excessive thermal mass associated with the alumina cement caused significant heat loss to the substrate, i.e., significant amounts of heat were dissipated before reaching the catalyst surface, thus producing a temperature gradient between the microheater and the catalyst surface. Removal of this passivation layer not only reduced the thermal mass of the sensor but also more effectively controlled the temperature of the catalytic layer, thereby improving the thermal resolution of the measurement when the catalyst interacted with an analyte. The catalyst layer is preferably 1.2 µm thick metal oxide catalyst layer. As previously mentioned, a variety of catalysts have been experimentally investigated for this purpose. Each of these thin-film materials were sputter-coated onto the thin film resistor and optimized for thickness to maximize catalytic sensitivity while maintaining the low mass characteristics of the microheater. Overall, embodiments of the fully fabricated microheater comprise a thickness of approximately 23.9 micrometers.

Figure 3:
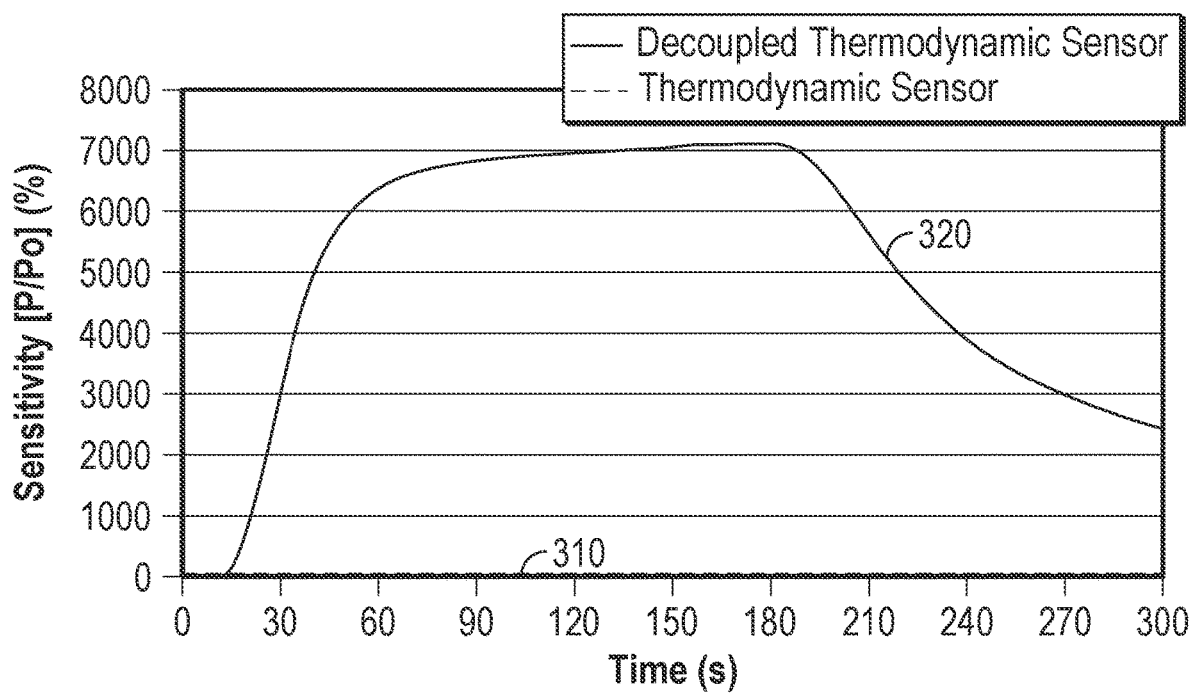
FIG. 3 shows an illustrative graphical representation which compares the response of a decoupled thermodynamic sensing platform to the previous thermodynamic sensing platform using 20 ppm triacetone triperoxide (TATP) as the analyte at an operating temperature of 175° C.

A comparison of different sensors is made in reference to FIG. 3. As illustrated, FIG. 3 compares response 310 of a previous thermodynamic sensing platform to response 320 of a decoupled thermodynamic sensing platform employing a tin oxide catalyst to 20 parts-per-million (ppm) TATP at an operating temperature of 175° C. The decoupled thermodynamic sensing platform outperformed earlier thermodynamic sensor platforms by several orders of magnitude: i.e., responses of 7000% compared to 20% were realized with the decoupled platform. This represents a 350× improvement in sensitivity relative to earlier thermodynamic sensing platforms. The performance of the decoupled thermodynamic sensing platform can be attributed to two factors. For one, the decoupling of the heating and sensing functions allows for detection of the target molecule at very low operating temperatures with minimal power requirements. The previous platform required approximately 450 mW to maintain an operating temperature of 175° C. whereas the decoupled thermodynamic sensing platform only required around 3 mW. The improved performance of the decoupled thermodynamic sensing platform was also attributed to its more efficient thermal characteristics. The microheater that was deposited on the back face of the substrate (exposed to moving air) acts as an insulator, thus, forcing heat transfer in the z-direction (towards the thin film sensor). This unique anisotropic behavior enables unique heating characteristics of the resistors and thus, increased efficiency compared to the previous thermodynamic platforms. The decoupled thermodynamic sensing platform has been used to detect a number of vapor phase analytes (explosives, narcotics, biological analytes, etc.) at trace levels with unprecedented sensitivity.

Figure 4:
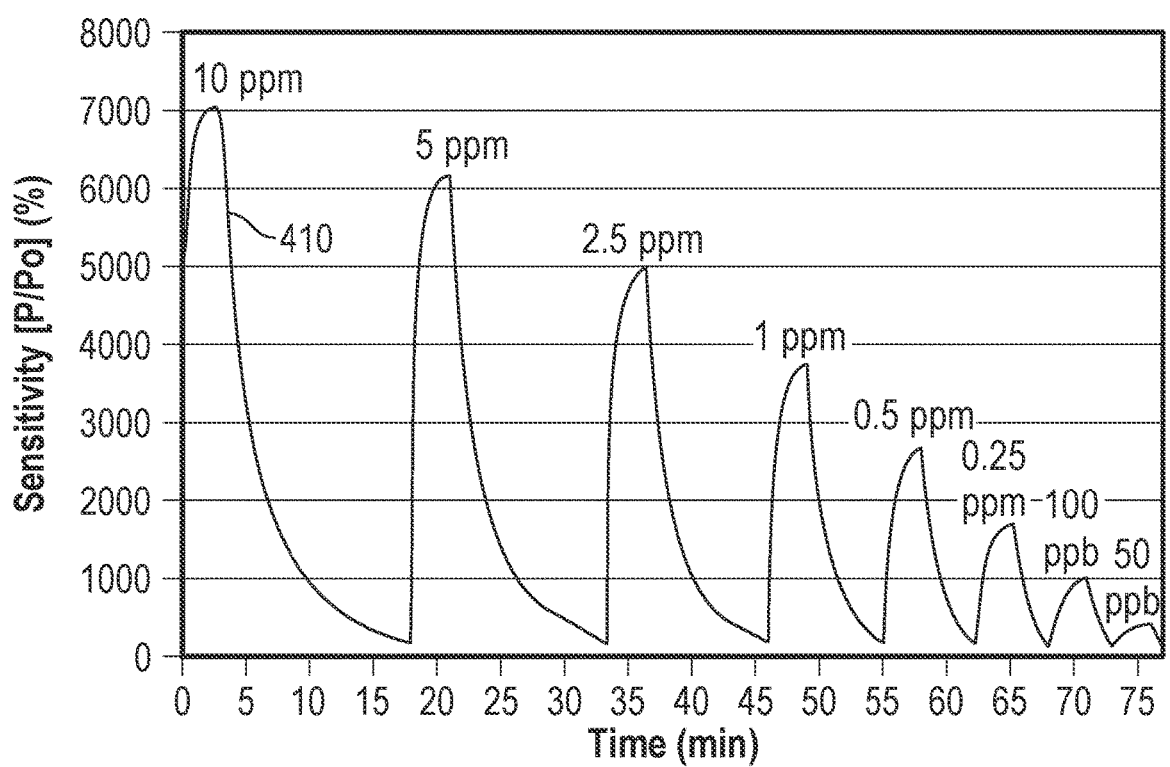
FIG. 4 shows an illustrative graphical representation which displays the response of a decoupled thermodynamic sensing platform to TATP at a variety of concentrations using an operating temperature of 175° C.

FIG. 4 shows response 410 of the decoupled thermodynamic sensing platform to TATP employing a tin oxide catalyst at 175° C. at a variety of concentrations. Here, the sensor showed remarkable sensitivity (approximately 500% improvement over known systems) at the part-per-billion (ppb) level, which represents the dilution limit of the available testing apparatus. Based on these results, detection at the part-per-trillion level and lower is expected. Thus, calibration curves for either increasing or decreasing concentrations may be generated for the precise measurement of the concentration of a target molecule (or analyte) concentration in the vapor phase.

Figure 5:
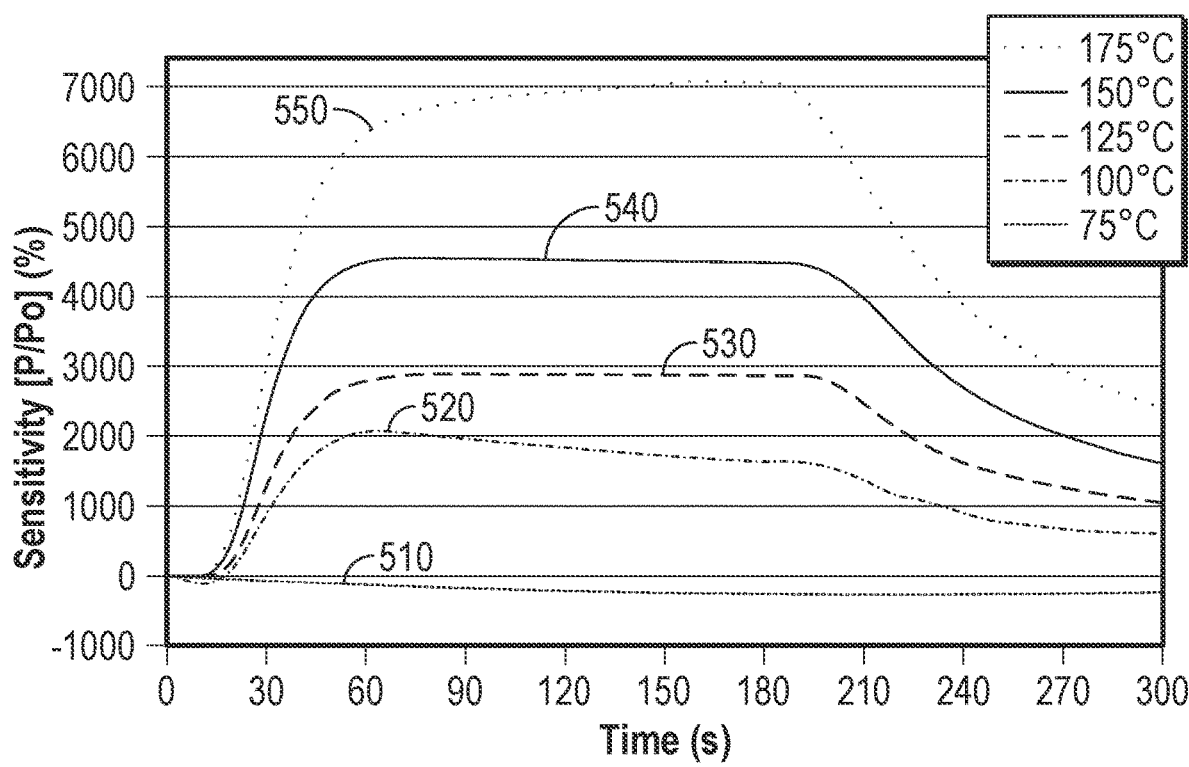
FIG. 5 shows an illustrative graphical representation which displays the response of a decoupled thermodynamic sensing platform to 20 ppm TATP operating at a variety of temperatures.

Due to the unparalleled sensitivity of the decoupled thermodynamic sensing platform, detection at very low operating temperatures was investigated. FIG. 5 shows the response of the decoupled thermodynamic sensing platform to 20 ppm TATP employing a tin oxide catalyst at a variety of operating temperatures. Specifically, response 510 to 75° C., response 520 to 100° C., response 530 to 125° C., response 540 to 150° C., and response 550 to 175° C. as shown. Here, the sensor continued to show remarkable sensitivity and selectivity at significantly lower operating temperatures when compared to the inventors' earlier thermodynamic sensor platform. The decoupled thermodynamic sensing platform showed a transition from exothermic reaction (oxidation) at 75° C. to endothermic reaction (reduction) at 100° C. and above. Traditionally, the sensitivities of the oxidation reactions are small (less than −5%) making them significantly harder to observe. However, the decoupled thermodynamic sensing platform displayed a sensitivity of −250% to the same oxidation reaction, which represents a 50× increase over previous platforms. Improved sensitivity to these exothermic reactions further improves the selectivity of the overall platform by allowing a single catalyst to be interrogated for multiple reactions.

Figure 6:
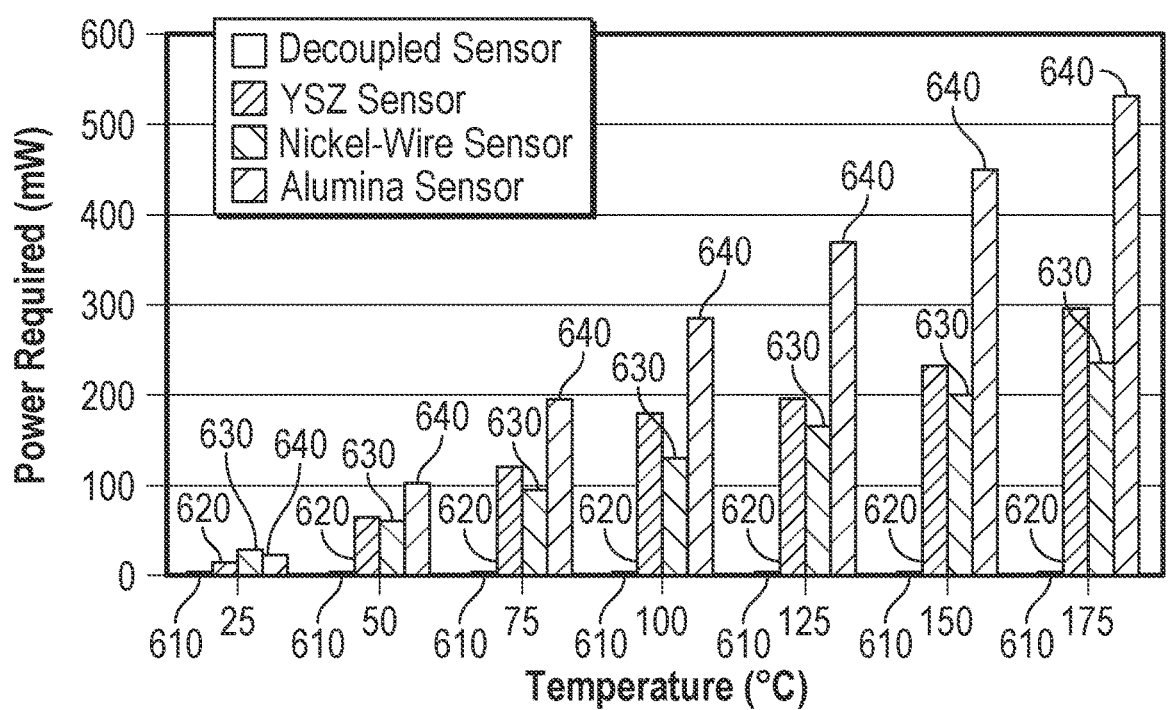
FIG. 6 shows an illustrative graphical representation which compares of the required power consumption of a decoupled thermodynamic sensing platform to other known thermodynamic sensors operating at a variety of temperatures.

As mentioned above, the decoupled thermodynamic sensing platform displays minimal power requirements due to the decoupling of the heating and sensing functionalities. FIG. 6 compares the required operating power of the decoupled thermodynamic sensing platform against previous sensing platforms. Here, the decoupled thermodynamic sensing platform is shown to require significantly less power at all temperatures. In particular, the power requirement of the decoupled sensor 610 was repeatedly shown to be much less than the power requirement of the YSZ sensor 620, power requirement of the nickel-wire sensor 630, and power requirement of the alumina sensor 640.

Figure 7:
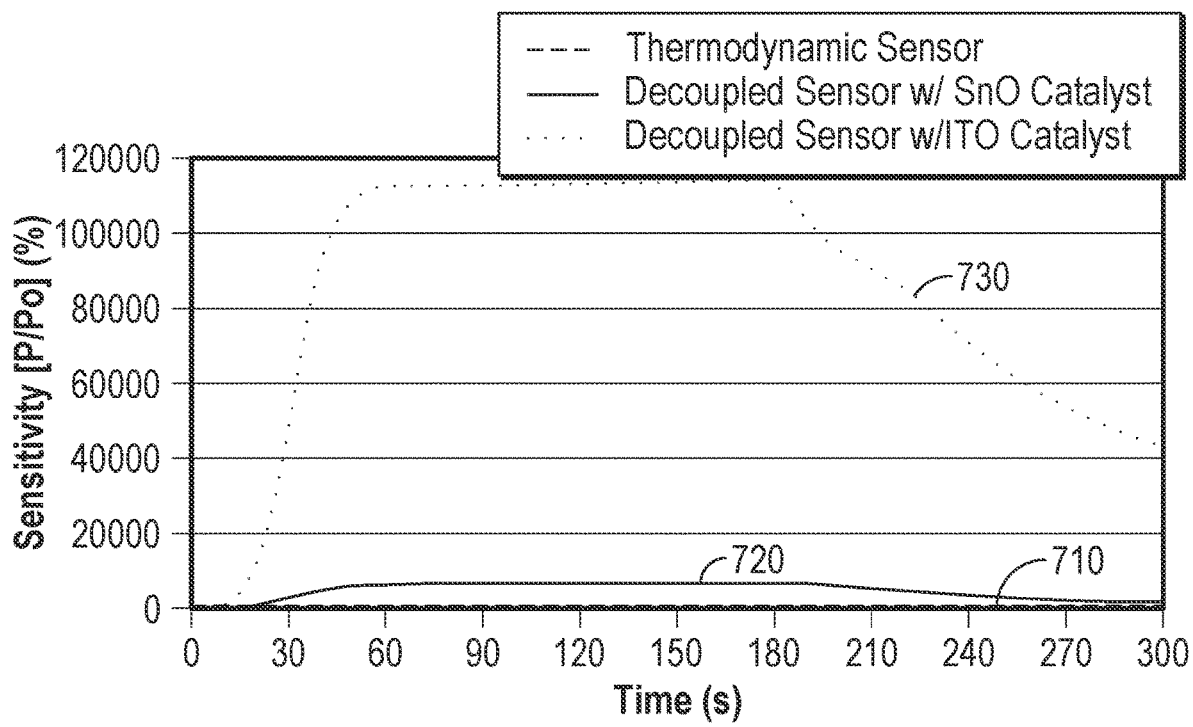
FIG. 7 shows an illustrative graphical representation which compares of the response of a decoupled thermodynamic sensing platform employing an indium tin oxide (ITO) catalyst and a SnO catalyst to another known thermodynamic sensing platform. Here, 20 ppm of the analyte (TATP) was detected by the sensor operating at a temperature of 175° C.

Decoupled thermodynamic sensing platforms employing a variety of catalysts have been fabricated. In addition to tin oxide, indium-tin-oxide catalysts have shown outstanding sensitivity to a number of target molecules. FIG. 7 compares response 710 of another known thermodynamic sensing platform to response 720 of a decoupled thermodynamic sensing platform employing a tin oxide catalyst and response 730 of a decoupled thermodynamic sensing platform employing an indium-tin-oxide catalyst to 20 ppm TATP at 175° C. Here, the indium-tin-oxide based decoupled thermodynamic sensing platform displayed even greater sensitivity: i.e., responses of approximately 115,000% were realized which is a 5750× increase in response over the previous thermodynamic sensor platform.

Figure 8:
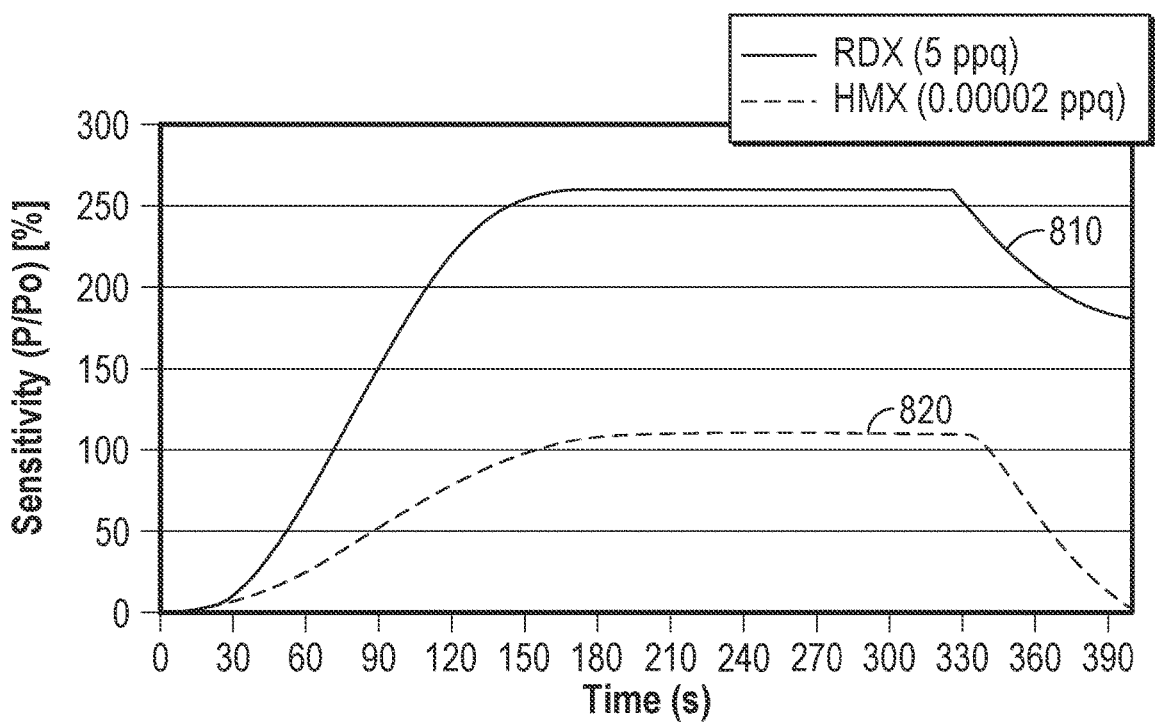
FIG. 8 shows an illustrative graphical representation of the response of a decoupled thermodynamic sensing platform to 5 ppq Royal Demolition eXplosive (RDX) and 0.00002 ppq High Melting Explosive (HMX) at an operating temperature of 175° C.

Based on the detection capabilities of the decoupled thermodynamic sensing platform, single molecule detection was demonstrated. In order to achieve detection at "single molecule" levels, ultra-low vapor pressure analytes were detected using the decoupled thermodynamic sensor system including plastic explosives such as Royal Demolition eXplosive (RDX) (1.55×10-12 atm) and High Melting Explosive (HMX) (2.8×10-17 atm). These explosives were then diluted to the limits of the available sampling apparatus resulting in vapor pressures of 5×10-15 atm and 2×10-20 atm for RDX and HMX respectively. These vapor pressures represent sub femtogram level quantities and thus, can be considered single molecule detection (SMD). FIG. 8 shows response 810 of a decoupled thermodynamic sensing platform to RDX and response 820 of the decoupled thermodynamic sensing platform to HMX at these SMD levels. Here, the decoupled thermodynamic sensing platform displayed sensitivities of approximately 100% and approximately 250% to HMX and RDX respectively.

Decoupled thermodynamic sensors have also been fabricated employing a variety of other metal oxide catalysts. These include aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), and tin oxide (SnO). Each catalyst displays different levels of sensitivity and selectivity based on the chemical reactions that result from the interaction with the target analyte.

Figure 9:
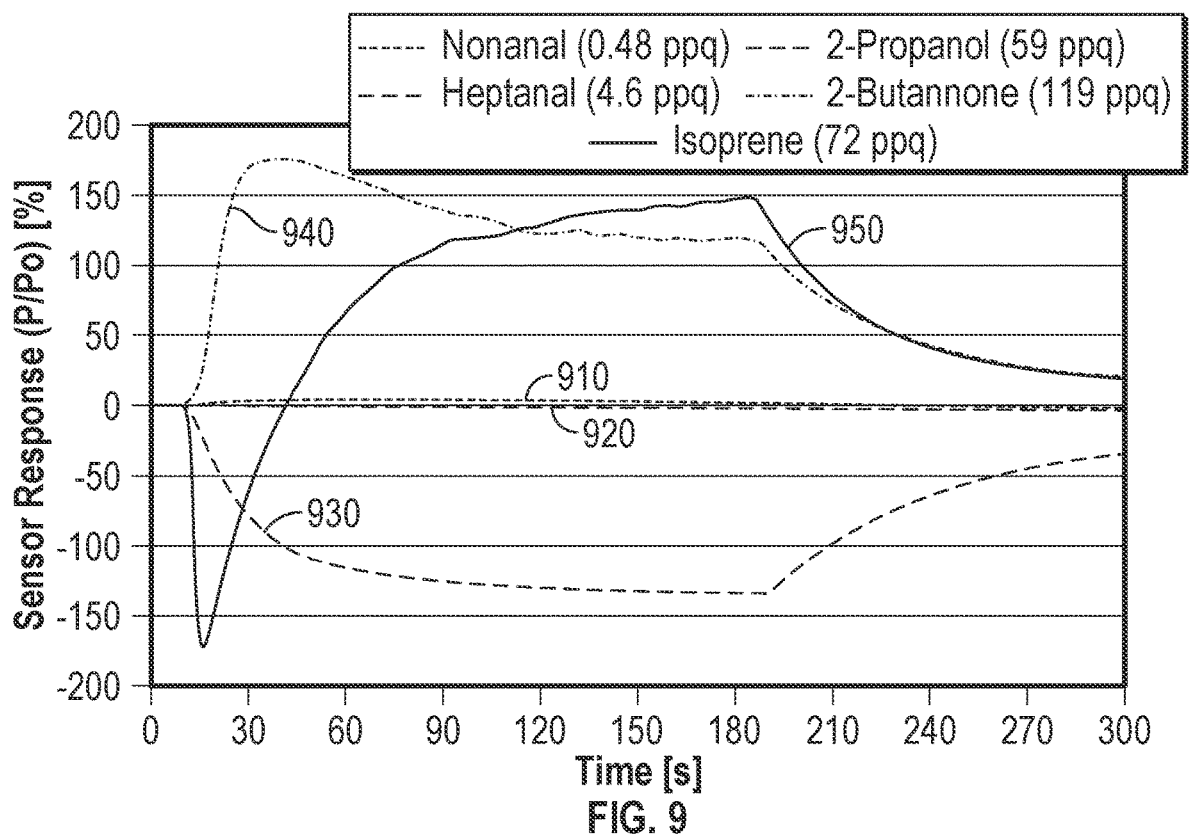
FIG. 9 shows an illustrative graphical representation of a comparison between responses of a decoupled thermodynamic sensor employing a $Al_2CuO_4$ catalyst to variety of analytes of different vapor pressures at an operating temperature of 250° C.

FIG. 9 shows a comparison of responses of a decoupled thermodynamic sensor employing a $Al_2CuO_4$ catalyst to a variety of analytes at an operating temperature of 250° C. The specific analytes are nonanal (0.48 ppq), heptanal (4.6 ppq), 2-propanol (59 ppq), 2-butanone (119 ppq), and isoprene (72 ppq). FIG. 9 shows response 910 of the decoupled sensor to nonanal (0.48 ppq), response 920 of the decoupled sensor to heptanal (4.6 ppq), response 930 of the decoupled sensor to 2-propanol (59 ppq), response 940 of the decoupled sensor to 2-butanone (119 ppq), and response 950 of the decoupled sensor to isoprene (72 ppq). $Al_2CuO_4$ displays highly selective responses to each analyte. $Al_2CuO_4$ shows positive (endothermic) responses to nonanal, 2-butanone and isoprene, a negative (exothermic) response to 2-propanol and is completely inert to heptanal. Similar responses are shown for manganese oxide and tungsten oxide (FIGS. 10 and 11 respectively), which are selectivity non-responsive to isoprene while also displaying a response to each of the other analytes. These selective responses represent the foundation for a highly selectivity decoupled thermodynamic sensor array for analyte "fingerprinting."

Figure 10:
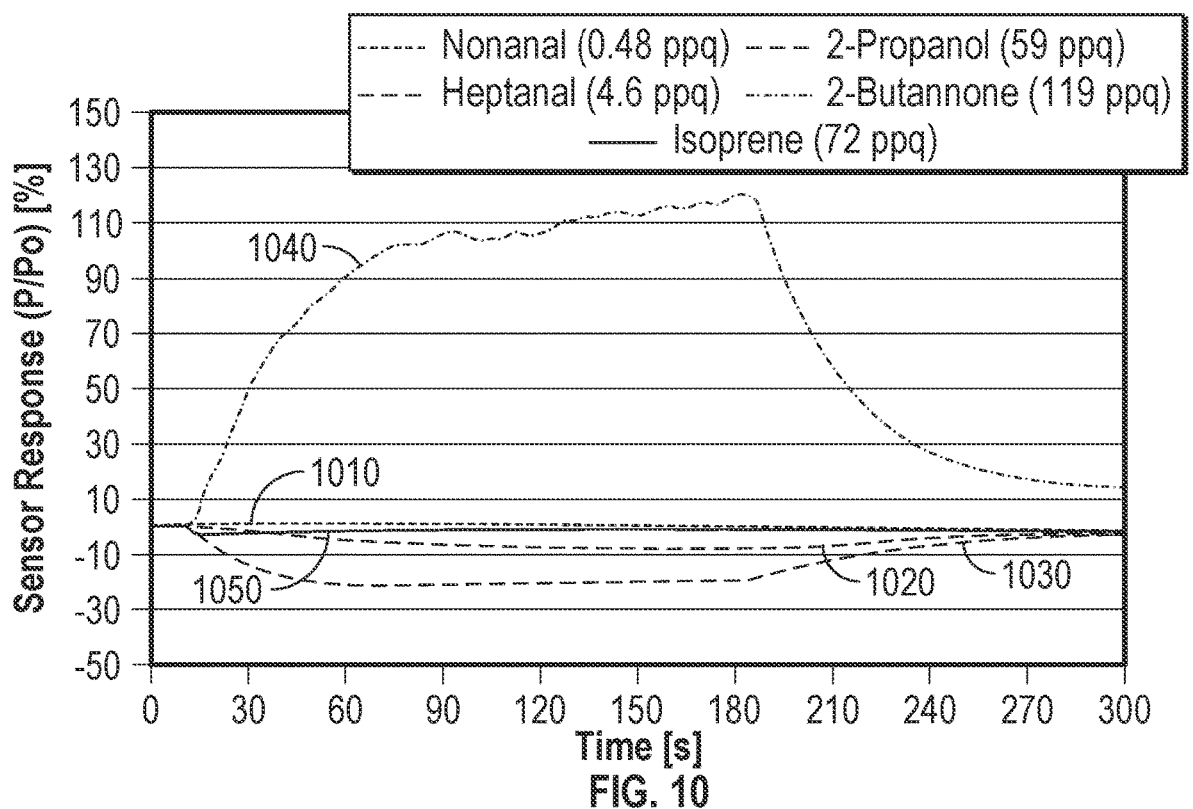
FIG. 10 shows an illustrative graphical representation of a comparison between responses of a decoupled thermodynamic sensor employing an MnO catalyst to variety of analytes of different vapor pressures at an operating temperature of 250° C.

FIG. 10 shows a number of responses of a decoupled thermodynamic sensor employing a manganese oxide catalyst to a variety of analytes. The specific analytes are nonanal (0.48 ppq), heptanal (4.6 ppq), 2-propanol (59 ppq), 2-butanone (119 ppq), and isoprene (72 ppq). FIG. 10 shows response 1010 of the decoupled sensor to nonanal (0.48 ppq), response 1020 of the decoupled sensor to heptanal (4.6 ppq), response 1030 of the decoupled sensor to 2-propanol (59 ppq), response 1040 of the decoupled sensor to 2-butanone (119 ppq), and response 1050 of the decoupled sensor to isoprene (72 ppq).

Likewise, FIG. 11 shows a number of responses of a decoupled thermodynamic sensor employing a tungsten oxide catalyst to a variety of analytes. The specific analytes are nonanal (0.48 ppq), heptanal (4.6 ppq), 2-propanol (59 ppq), 2-butanone (119 ppq), and isoprene (72 ppq). FIG. 11 shows response 1110 of the decoupled sensor to nonanal (0.48 ppq), response 1120 of the decoupled sensor to heptanal (4.6 ppq), response 1130 of the decoupled sensor to 2-propanol (59 ppq), response 1140 of the decoupled sensor to 2-butanone (119 ppq), and response 1150 of the decoupled sensor to isoprene (72 ppq).

Decoupled thermodynamic sensors in accordance with the present invention are well-suited for an array platform capable of selective detection and identification of a library of vapor phase analytes. The highly anisotropic heating properties of the YSZ substrates allow for easy integration of more than ten or more microheaters and sensors (including a reference) on a single substrate with no appreciable thermal communication. An array of this type could be quantitative or qualitative depending on the desired application. It will be appreciated that if a plurality of decoupled thermodynamic sensors share a common substrate, then the individual substrates of each sensor are contiguous with the substrates of the other commonly mounted sensors. FIG. 12A illustrates an embodiment of sensor array 1200 having N sensors and one reference sensor. Specifically, first sensor 1205, second sensor 1210, and other sensors up to and including Nth sensor 1215 are all mounted on substrate 1220. Reference sensor 1225 is also mounted on substrate 1220.

In other preferred embodiments, decoupled thermodynamic sensors comprise a plurality of microheaters and sensors that do not share a common substrate. For example, a device may include a plurality of microheaters and sensors (including a reference), each with its own substrate to further prevent thermal communication. FIG. 12B illustrates an embodiment of sensor array 1250 having N sensors and one reference sensor. Specifically, first sensor 1255, second sensor 1260, and other sensors up to and including Nth sensor 1265, as well as reference sensor 1270 each are mounted on separate substrates 1275, 1280, 1285, 1290. It will be appreciated that in embodiments wherein the sensors do not share a common substrate, advantages include increased configuration options, including the ability to position the sensors in different locations relative to one another and facilitated replacement options wherein a subset of a group of sensors may be replaced with other sensors having the same or different catalysts.

Sensor arrays, such as those depicted in FIG. 12A and FIG. 12B, display remarkable flexibly and may be placed in a variety of orientations and at any distance with significantly reduced thermal communication between sensors as compared to known systems. In practice, the controller of the sensor is used to heat each microheater individually to a pre-determined temperature setpoint. Upon or after reaching the desired setpoint temperature, the thin-film sensor layers are allowed to reach thermal equilibrium with the microheater layers before activation. The catalyst coated sensors and reference sensor are exposed to a target analyte, preferably this exposure occurs approximately simultaneously. The individual redox reactions on the surface of each catalyst results in heat effects which are determined by the controller based on the power usage of the sensors. Each measurement is then compared to (e.g., subtracted from) the reference measurement to help mitigate any false positives or false negatives. An array of separate sensors, such as those illustrated in FIG. 12B, could be incorporated into a variety of standalone devices including wearables, breathalyzers, scanning wands, etc. Additionally, the low mass and low power requirements facilitates the use of an array of sensors onboard a variety of mobile platforms including drones, robots, and UAVs.

Upon interaction with the target analyte, each catalyst has the potential for three distinct responses. As mentioned above, reduction reactions produce positive (+) responses while oxidation reactions produce negative (−) responses. A catalyst may also be unresponsive to a target analyte, indicating the absence of any catalytic decomposition/redox reactions and thus, no response (NR). A "fingerprint" may be constructed for each target analyte based on the response of each catalyst. Thus, a set of pre-determined catalysts can be chosen to allow "selective" identification of each analyte.

The sensor arrays depicted in FIG. 12A and FIG. 12B, like other embodiments disclosed herein, may be configured to be quantitative and qualitative as desired. In another embodiments, sensor arrays can measure the magnitude of each thermodynamic response and provide real-time measurement of the analyte concentration in addition to rapid identification of the analyte.

FIG. 13 shows summary table of data 1300 containing the thermodynamic sign (positive or negative), and thus an indication of the measured redox reactions, for six distinct catalysts making up an embodiment of a decoupled thermodynamic sensor array. The table shows that each of the 14 analytes (acetone (10 ppm), ammonium nitrate (AN) (14 ppb), RDX (7 ppt), $H_2O_2$ (7 ppm), TATP (20 ppm), DADP (50 ppm), and 2,4-DNT (180 ppb), CBD (13 ppt), THC (0.15 ppt), glucose (80 ppq), fructose (15 ppt), ammonia (7 ppm), natural gas (7 ppm), and methanol (15 ppm)) possess distinct "fingerprints" when the reaction results for each of the six sensors are compared, and these "fingerprints" may be used for rapid identification. Thus, a decoupled thermodynamic sensor array formed using some or all of the catalysts in the table could be used to detect an analyte. A decoupled thermodynamic sensor array could also identify which of the 14 analytes was present based on a determination of whether the reaction at individual sensors was endothermic or exothermic and a comparison of the results of the catalysts to the data in the summary table. The data in FIG. 13 may be stored in a database accessible by the controller of a sensor array, and thus, the sensor array may compare heat effects of its sensors to the database of known reactions (known analytes) in order to identify the existence and/or concentration of a particular analyte. Such databases of reactions (with known analytes) using difference catalysts may include the identification of essential and optional catalysts that provide additional flexibility to the sensor array platform by allowing configuration to detect one or more specific analytes, such as a group of analytes associated with explosives. The essential catalysts allow for easy identification of the target analyte while the optional catalysts can be added or removed for redundancy. It will be appreciated that the data of the summary table could be expanded through further testing with numerous analytes and the addition of other potential catalysts. Thus, the data in the database of the summary table is not limited to the catalysts or analytes identified therein.

The sensor array platform is unique in that the quantity and composition of the catalysts can be modified based on the desired application. In some embodiments, the sensor array can be configured for the detection of explosives, explosive precursors, narcotics, drugs, hallucinogenic and non-hallucinogenic compounds, and a variety of other VOCs. For example, FIG. 13 depicts summary table of data 1300 from a database presented in a tabular form illustrating reaction results of a sensor array having of six catalyst sensors (namely, $Al_2CuO_4$, $Fe_2O_3$, ITO, MnO, SnO, and WO). Sensor arrays including these six catalysts are well-suited for selectively identifying analytes having unique "fingerprints" that are identified as being one of least five explosives, two explosive precursors, one hallucinogenic compound, one non-hallucinogenic compound, and at least five additional compounds. The number of detectable analytes may be selectively increased through further testing and the addition of more sensors having different catalysts. Sensor arrays that include the catalysts identified in FIG. 13 may be deployed onboard a variety of wearables, vehicles (cars, drones, UAVs), and robots to detect explosives in airports, warzones, or any densely populated venues. Sensor arrays including the catalysts identified in FIG. 13 are also well-suited to be deployed by law enforcement in breathalyzers for the detection of THC, as well as by border patrol officers or "TSA Screeners" in a "scanning wand" for the identification of drugs and other illicit materials. Such sensor arrays may be used, for example, as part of a stationary system for the detection of natural gas leaks in homes and industrial settings.

In yet other embodiments, sensor arrays may be configured for the detection of biomarkers for a variety of healthcare applications including breathalyzers and wearables.

FIG. 14 depicts a summary table of data 1400 from a database presented in tabular form illustrating reactions with known analytes of a sensor array having seven catalysts (namely $Al_2CuO_4$, CuO, $Fe_2O_3$, ITO, MnO, SnO, and WO). Sensor arrays that include sensors having these catalysts are well-suited for selectively identifying and differentiating between acetone, glucose, fructose, ammonia, $H_2O_2$, nonanal, heptanal, ethylbenzene, 2-propanol, 2-butanone, and isoprene, thereby providing beneficial diagnostic applications. Acetone and glucose vapors have been correlated to blood glucose at known concentrations. Thus, sensor arrays having a configuration of sensors as indicated in FIG. 14 may be deployed as part of a wearable or as a breathalyzer allowing for noninvasive glucose measurement for diabetics. In one embodiment, an array of decouple thermodynamic sensors may be deployed as part of a pet collar for continuous, non-invasive monitoring of blood glucose levels for diabetic pets. Similarly, ammonia is a known biomarker for chronic kidney disease (CKD). Thus, sensor arrays having a configuration of sensors as indicated in FIG. 14 may be used as part of a breathalyzer for rapid, real-time diagnosis. Moreover, $H_2O_2$ is present in wounds during the healing process. A bandage employing a sensor array having the six catalysts identified in FIG. 14 may measure $H_2O_2$ levels in the wound and provide real-time monitoring of wound healing for first responders. Additionally, nonanal, heptanal, ethylbenzene, 2-propanol, 2-butanone, and isoprene are widely considered breath and skin biomarkers for cancer patients. Thus, sensor arrays having a configuration of sensors as indicated in FIG. 14 may be deployed as part of a wearable or as a breathalyzer allowing for continuous, noninvasive cancer screening and diagnosis. Overall, the decoupled thermodynamic sensing system has been used to detect breath, skin, and sweat biomarkers related to variety of chronic and acute diseases (including diabetes, chronic kidney disease (CKD), Alzheimer's, and cancer).

The tables shown in FIGS. 13 and 14 depict qualitative examples of data from one or more databases of reaction results of various analytes when exposed to sensors having different catalysts. Such data, when used with a sensor array having sensors with pre-selected catalysts, may be used for the selective identification of analytes by the thermodynamic sensor array. It will be appreciated that the data results identified in these tables represents only a sample of the data collected and that additions to the database may be made through further testing with additional analytes and/or sensors having other catalysts. The tables of FIGS. 13 and 14 also represent data that may be used (and expanded on) as part of a database for a sensor platform capable of detecting selected analytes.

It will be appreciated that some embodiments of a sensor array may be special purpose detection devices having sensors with catalysts that are selectively chosen to target one or more analytes falling within a certain category (e.g., explosives, drugs and narcotics, biomarkers, etc.). Likewise, other embodiments may contain a larger number of sensors and may be capable of serving as a general-purpose detection device, wherein the device may be capable of detecting and differentiating between analytes from a plurality of categories.

Figure 15:
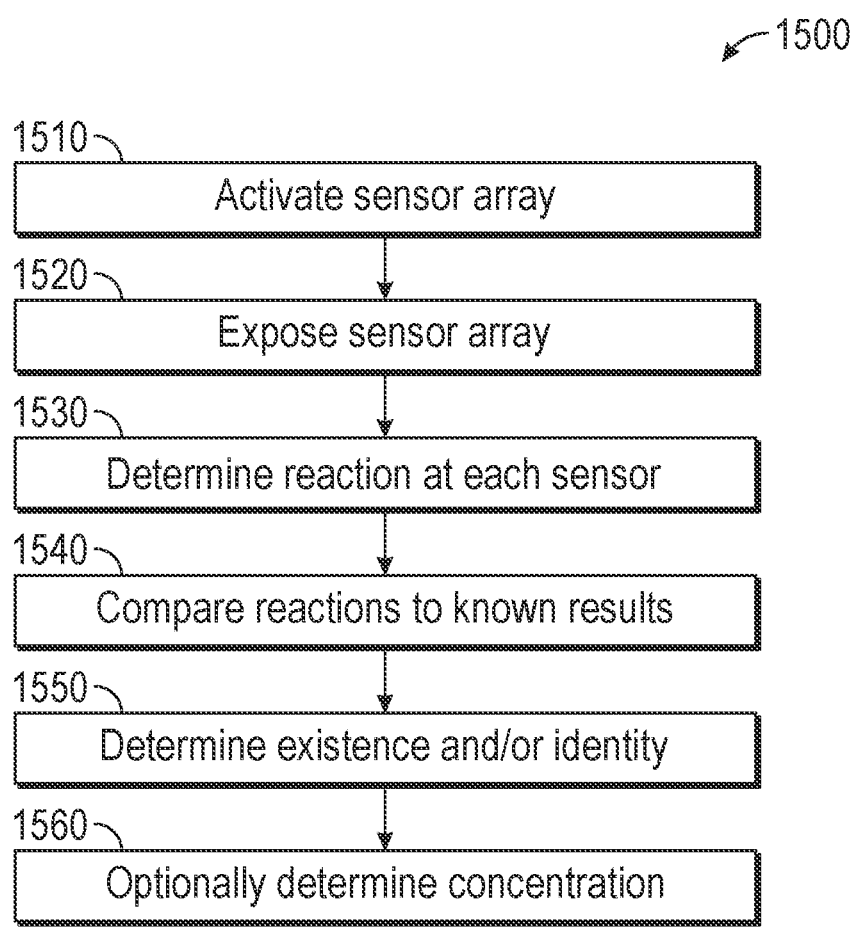
FIG. 15 shows an example of a method of using a decoupled sensor array to detect an analyte.

Exemplary method 1500 of using an embodiment of a sensor array is described in reference to FIG. 15. Method 1500 may be used to determine the existence and/or identity of an analyte and, optionally, the concentration of an analyte. The method begins at step 1510 in which a user has a sensor array with multiple sensors, such as sensor array 1200 or sensor array 1250. The sensor array is activated by providing power to some or all of the decoupled microheaters (including one or more reference sensors) so that the temperature of the microheater of each activated sensor is raised to the desired setpoint temperature. It will be appreciated that each of the microheaters need not have the same temperature setpoint, and in operation the sensor array may include sensors operating at different temperature setpoints. In some embodiments, in which the sensors have different setpoint temperatures, a plurality of reference sensors may be provided wherein a reference sensor may be provided for each of the different temperature setpoints and used as a reference point for the microheaters having corresponding temperatures. As described herein, the temperature of the microheater may be adjusted through the delivery of power, wherein the addition of power increases the temperature, while the reduction of power lowers the temperature. The decoupled microheater is allowed to reach thermal equilibrium with the corresponding thin-film sensor. The YSZ substrate possesses highly anisotropic thermal properties such that the decoupled microheater and thin-film sensor should have a temperature difference of less than 1° C. The thermodynamic thin-film sensor for each catalyst and the corresponding reference sensor is then activated. At step 1520, the sensor array is exposed to an environment in which knowledge of the existence, identity, or concentration of an analyte is desired. For example, the sensor array may be attached to a drone and flown in a battlefield, or mounted in a fixed location at an airport, or provided on a mobile platform that may be worn or carried by a user. When the sensor array is provided in such an environment in which an analyte is present, the analyte reacts with one or more of the sensors in the array.

At step 1530, the reaction at each of the sensors is determined. An exothermic reaction at a sensor will produce heat and the corresponding power required to maintain the sensor at the setpoint temperature will be reduced. Likewise, in response to an endothermic reaction, more power will have to be provided to the sensor to maintain the setpoint temperature. The determination of the reaction at each sensor may be quantitative, in which a determination is made of whether the reaction is endothermic, exothermic, or neither. Additionally, readings of the qualitative magnitude of the power change may be obtained.

At step 1540, the reactions at one or more sensors are compared to known results (database for specific analytes and catalysts). In preferred embodiments, the sensor array is in communication with a database of known results (database for specific analytes and catalysts). and a comparison the sensors responses to the known results may be automated. At step 1550, a determination is made as to the existence and/or the identity of an analyte based on the comparison of sensor responses to known reaction results. For example, consider a sensor array for detecting drugs configured with the six catalysts corresponding to FIG. 13. If the sensor having the indium-tin-oxide catalyst indicates that an endothermic reaction occurred (requiring the addition of power to maintain the setpoint temperature), a determination may be made that CBD or THC may be present, as each of these produces an endothermic reaction to the sensor with indium-tin-oxide. However, though the results from that single sensor may indicate the presence of a drug, results from additional sensors are required to identify the analyte. For example, if the sensors having the tin oxide and tungsten oxide catalysts each indicate an endothermic reaction, whereas the sensors having the $Al_2CuO_4$, $Fe_2O_3$, and CuO sensors each indicate an exothermic reaction, then a determination may be made that the identity of the analyte is THC. It will be appreciated that due to the "fingerprints" of the various analytes, an identification may be made of some analytes by using less than six sensors.

Some embodiments may include optional step 1560, in which a determination is made of the concentration of the analyte. Here, qualitative data is compared to known results. For example, the change in the power provided to the sensors and the amount of that power may be compared to known results to provide an indication of the concentration of the detected analyte. For example, a rapid change in the power required to operate a sensor may be indicative of a higher concentration of the detected analyte, whereas a more gradual change in the required power is indicative of a lower concentration of the analyte. Graphical results demonstrating the differences in response time and intensity associated with various concentrations of TATP are shown in FIG. 4. It will be appreciated that a database of known sensor responses with comparable results to other analytes to which sensor responds may be used for purposes of determining the concentration of the analyte.

Overall, decoupled thermodynamic sensors employing ultrathin YSZ substrates and Pd-based microheaters display the ability to detect a multitude of compounds in the vapor at the single molecule level both continuously and in real-time.

While preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention.

The invention claimed is:

1. A detection device comprising:
    a sensor comprising:
        a first layer comprising a metallic microheater,
        a second layer in contact with the first layer, the second layer comprising a substrate,
        a third layer in contact with the second layer, the third layer comprising a thin-film sensor, and
        a fourth layer in contact with the third layer, the fourth layer comprising a catalyst,
        wherein the thin-film sensor is configured to detect a heat effect resulting from a chemical reaction.

2. The detection device of claim 1, wherein the metallic microheater is copper.

3. The detection device of claim 1, wherein the thin-film sensor is palladium.

4. The detection device of claim 1, wherein the catalyst is a metal oxide catalyst.

5. The detection device of claim 1, wherein the substrate is yttria-stabilized-zirconia.

6. The detection device of claim 1, wherein the substrate has a thickness of less than 40 micrometers.

7. The detection device of claim 1, wherein the substrate provides a passivation layer between the metallic microheater and the thin-film sensor.

8. The detection device of claim 1, wherein the sensor is configured to detect an analyte in a vapor phase based on the heat effect.

9. The detection device of claim 8, wherein the sensor is configured to detect the analyte at concentration levels as low as a single molecule of the analyte.

10. The detection device of claim 1, further comprising a controller in communication with the sensor.

11. The detection device of claim 10, further comprising a reference sensor in communication with the controller.

12. The detection device of claim 10, further comprising a second sensor in communication with the controller, the second sensor comprising a second catalyst.

13. The detection device of claim 12, further comprising a third sensor comprising a third catalyst, a fourth sensor comprising a fourth catalyst, and a fifth sensor comprising a fifth catalyst, each of the third sensor, fourth sensor, and fifth sensor in communication with the controller.

14. The detection device of claim 13, wherein the catalyst comprises aluminum copper oxide ($Al_2CuO_4$), the second catalyst comprises iron oxide ($Fe_2O_3$), the third catalyst comprises indium-tin oxide (ITO), the fourth catalyst comprises tin oxide (SnO), and the fifth catalyst comprises tungsten oxide (WO).

15. The detection device of claim 14, further comprising a sixth sensor comprising a sixth catalyst selected from copper oxide (CuO) or manganese oxide (MnO).

16. A detection device comprising:
a first sensor comprising a first microheater, a first thin-film sensor, and a first catalyst in thermal communication with the first thin-film sensor, the first microheater separated from the first thin-film sensor by a substrate;
a second sensor comprising a second microheater layer, a second thin-film sensor, and a second catalyst layer in thermal communication with the second thin-film sensor, the second microheater separated from the second thin-film sensor;
a controller in communication with the first sensor and the second sensor, the controller configured to:
cause a first amount of power to be provided to the first and second microheaters to heat the first thin-film sensor to a first setpoint temperature and to heat the second thin-film sensor to a second setpoint temperature;
in response to an endothermic reaction at the first or second sensor, cause a second amount of power to be applied to at least one of the first sensor or the second sensor to maintain the first setpoint temperature and the second setpoint temperature;
determine a measurement of the difference between the first amount of power and the second amount of power, and
determine an existence, identity, and/or concentration of the analyte based on the measurement.

17. The detection device of claim 16, wherein the first setpoint temperature is the same as the second setpoint temperature.

18. The detection device of claim 16, further comprising a reference sensor comprising a reference microheater and a reference thin-film sensor, the reference sensor in communication with the controller.

19. The detection device of claim 16, further comprising:
a third sensor comprising a third microheater, a third thin-film sensor, and a third catalyst in thermal communication with the third thin-film sensor;
a fourth sensor comprising a fourth microheater, a fourth thin-film sensor, and a fourth catalyst in thermal communication with the fourth thin-film sensor; and
a fifth sensor comprising a fifth microheater, a fifth thin-film sensor, and a fifth catalyst in thermal communication with the fifth thin-film sensor.

20. The detection device of claim 19, wherein the first catalyst comprises aluminum copper oxide ($Al_2CuO_4$), the second catalyst comprises iron oxide ($Fe_2O_3$), the third catalyst comprises indium-tin oxide (ITO), the fourth catalyst comprises tin oxide (SnO), and the fifth catalyst comprises tungsten oxide (WO).

21. The detection device of claim 20, further comprising a sixth decoupled sensor comprising a sixth catalyst comprises copper oxide (CuO) or manganese oxide (MnO).

22. The detection device of claim 19, wherein the first catalyst, the second catalyst, the third catalyst, the fourth catalyst, and the fifth catalyst each comprise at least one of aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), or tin oxide (SnO).

23. The detection device of claim 16, wherein the setpoint temperature is between 50° C. and 500° C.

24. The detection device of claim 16, wherein the second microheater is separated from the second thin-film sensor by the substrate.

25. The detection device of claim 16, wherein the second microheater is separated from the second thin-film sensor by a second substrate.

26. A method of detecting an analyte, the method comprising:
providing a sensor array, the sensor array comprising:
a first sensor comprising a first microheater layer, a first substrate layer coupled to the first microheater layer, a first thin-film sensor coupled to the substrate layer, and a first catalyst layer coupled to the first thin-film sensor; and
a second sensor comprising a second microheater layer, a second substrate coupled to the second microheater layer, a second thin-film sensor coupled to the second substrate, and a second catalyst layer coupled to the second thin-film sensor;
delivering a first amount of power to the sensor array to heat the first thin-film sensor to a first setpoint temperature and to heat the second thin-film sensor to a second setpoint temperature;
exposing the sensor array to an analyte to permit a reaction between the analyte and the sensor array;
in response to the reaction, delivering a second amount of power to the sensor array to maintain the first setpoint temperature and the second setpoint temperature;
determining a measurement of the difference between the first amount of power and the second amount of power; and
determining an existence, identity, and/or concentration of the analyte based on the measurement.

27. The method of claim 26, wherein the first setpoint temperature and the second setpoint temperature are each between 50° C. and 500° C.

28. The method of claim 26, wherein determining an existence, identity, and/or concentration of the analyte based on the measurement further comprises comparing the measurement to a database of known thermal responses.

29. The method of claim 26, wherein the sensor array further comprises a reference sensor and wherein determining the determining an existence, identity, and/or concentration of the analyte based on the measurement comprises comparing the measurement to a third amount of power delivered to the reference sensor.

30. The method of claim 26, wherein the first catalyst layer comprises at least one of aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), or tin oxide (SnO).

* * * * *